(12) United States Patent
Fisher et al.

(10) Patent No.: US 12,390,202 B2
(45) Date of Patent: Aug. 19, 2025

(54) TELESCOPING NEEDLE ASSEMBLY WITH SIDE CUTTING NEEDLE

(71) Applicant: Praxis Holding LLC, Tampa, FL (US)

(72) Inventors: John Steele Fisher, Belleair, FL (US); Nathaniel H. Pariseau, Tampa, FL (US); Elizabeth A. Fisher, Tampa, FL (US); Wayne A. Noda, Mission Viejo, CA (US); Andrew D. Palmer, Winter Springs, FL (US); Victor M. De Marco, Orlando, FL (US)

(73) Assignee: Praxis Holding LLC, Tampa, FL (US)

( * ) Notice: Subject to any disclaimer, the term of this patent is extended or adjusted under 35 U.S.C. 154(b) by 924 days.

(21) Appl. No.: 17/545,065

(22) Filed: Dec. 8, 2021

(65) Prior Publication Data

US 2022/0087657 A1  Mar. 24, 2022

Related U.S. Application Data

(63) Continuation-in-part of application No. 17/241,327, filed on Apr. 27, 2021, now Pat. No. 11,737,737, and a continuation of application No. PCT/US2020/054982, filed on Oct. 9, 2020, which is a continuation of application No. 17/066,031, filed on Oct. 8, 2020, now Pat. No. 11,849,927.

(60) Provisional application No. 63/122,671, filed on Dec. 8, 2020, provisional application No. 62/913,015, filed on Oct. 9, 2019.

(51) Int. Cl.
| | | |
|---|---|---|
| A61B 10/02 | (2006.01) | |
| A61B 8/12 | (2006.01) | |
| A61B 17/34 | (2006.01) | |
| A61B 1/018 | (2006.01) | |
| A61B 10/04 | (2006.01) | |
| A61B 17/00 | (2006.01) | |

(52) U.S. Cl.
CPC ............ *A61B 10/0266* (2013.01); *A61B 8/12* (2013.01); *A61B 17/3476* (2013.01); *A61B 1/018* (2013.01); *A61B 2010/0208* (2013.01); *A61B 2010/045* (2013.01); *A61B 2017/00991* (2013.01); *A61B 2017/3413* (2013.01)

(58) Field of Classification Search
None
See application file for complete search history.

(56) References Cited

U.S. PATENT DOCUMENTS

| | | |
|---|---|---|
| 4,381,777 A | 5/1983 | Garnier |
| 5,151,089 A | 9/1992 | Kirk, III et al. |

(Continued)

FOREIGN PATENT DOCUMENTS

WO  2019155472 A1  8/2019

OTHER PUBLICATIONS

International Search Report for PCT/US20/54982 filed on Oct. 9, 2020, mailing date Feb. 17, 2021.

(Continued)

*Primary Examiner* — Benjamin S Melhus
(74) *Attorney, Agent, or Firm* — Nicholas Pfeifer; Smith & Hopen, P. A.

(57) ABSTRACT

A telescoping assembly such as an endobronchial ultrasound needle (EBUS) assembly includes a motor coupled to a biopsy needle within a telescoping housing to rotate (such as to oscillate) the needle during tissue harvest to improve harvesting.

20 Claims, 27 Drawing Sheets

(56) References Cited

U.S. PATENT DOCUMENTS

| | | |
|---|---|---|
| 2009/0118641 A1 | 5/2009 | Van Dam et al. |
| 2009/0326412 A1 | 12/2009 | Pakter |
| 2015/0201917 A1* | 7/2015 | Snow .................. A61B 10/0266 600/567 |
| 2017/0055967 A1 | 3/2017 | Raybin et al. |
| 2021/0038202 A1 | 2/2021 | Klein et al. |

OTHER PUBLICATIONS

Supplemental Partial European Search Report for EP application No. 20873633, received on Sep. 13, 2023.

* cited by examiner

SECTION A-A

DETAIL B

TELESCOPING NEEDLE ASSEMBLY WITH SIDE CUTTING NEEDLE

CROSS-REFERENCE TO RELATED APPLICATIONS

This nonprovisional application is a continuation in part of and claims priority to nonprovisional application Ser. No. 17/241,327, entitled TELESCOPING NEEDLE ASSEMBLY WITH ROTATING NEEDLE, filed Apr. 27, 2021 by the same inventor(s), which is a continuation of and claims priority to nonprovisional application No. 17/066,031, entitled TELESCOPING NEEDLE ASSEMBLY WITH ROTATING NEEDLE, filed Oct. 8, 2020 by the same inventor(s), which claims priority to provisional application No. 62/913,015, entitled "BIOPSY NEEDLE," filed Oct. 9, 2019 by the same inventor(s).

This nonprovisional application also claims priority to PCT application number PCT/US20/54982, entitled TELESCOPING NEEDLE ASSEMBLY WITH ROTATING NEEDLE, filed Oct. 9, 2020 by the same inventor(s), which claims priority to nonprovisional application No. 17/066,031, entitled TELESCOPING NEEDLE ASSEMBLY WITH ROTATING NEEDLE, filed Oct. 8, 2020 by the same inventor(s), and provisional application No. 62/913,015, entitled "BIOPSY NEEDLE," filed Oct. 9, 2019 by the same inventor(s).

This nonprovisional application also claims priority to provisional application number 63/122,671, entitled "BIOPSY NEEDLE WITH CUTTING STRUCTURE AND RELATED METHOD OF MANUFACTURE," filed Dec. 8, 2020 by the same inventor(s).

BACKGROUND OF THE INVENTION

1. Field of the Invention

The application relates generally to syringe systems, and more particularly to biopsy syringe systems with rotating needles.

2. Brief Description of the Prior Art

It may be necessary to extract tissue from a patient for analysis to support diagnosis. For example, it may be necessary to extract tissue for "cytological" or cell harvest, as well as cores of tissue for breast biopsies, to ascertain the existence of disorders of the tissue.

Tissue extraction may be done by inserting a needle into the patient to withdraw tissue into a syringe connected to the needle, which is then used for dispensing the tissue onto analysis equipment.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

In the present assignee's co-pending U.S. Pat. No. 10,765,411 and U.S. patent application Ser. No. 16/013,522, both incorporated herein by reference, motorized tissue extraction devices are disclosed that conveniently avoid multiple needle insertions in the patient to obtain sufficient tissue for analysis while harvesting sufficient tissue for analysis.

Present principles are directed to extending techniques described in the referenced patent documents to telescoping assemblies such as endobronchial ultrasound needle (EBUS) applications, which are used to obtain tissue samples of lymph nodes in the lung.

Accordingly, an endobronchial ultrasound needle (EBUS) assembly includes a housing with at least first and second segments coupled telescopically. The EBUS assembly includes at least one hollow needle supported by the housing, and at least one motor in the housing and geared to the needle to cause the needle to rotate.

In example embodiments a sheath surrounds the needle and can move axially with the needle, while a stylet may extend through the needle prior to tissue harvesting to impede epithelial tissue from entering the needle prior to biopsy of tumor tissue.

In some embodiments the housing has at least three segments coupled telescopically.

In example implementations a power supply in the housing is connected to the motor to energize the motor. In such implementations a manipulable actuator may be provided on the housing to energize the motor.

In some examples a first manipulable mechanical stop is on the housing and is movable from a first position, in which the first and second segments can telescope relative to each other, and a second position, in which the first and second segments cannot telescope relative to each other. The first manipulable mechanical stop may include a thumb screw. A second manipulable mechanical stop may be on the housing and may be movable to lock second and third telescoping segments together.

In another aspect, a telescoping assembly includes a housing with at least first and second segments coupled telescopically. At least one hollow needle is supported by the housing, and at least one motor in the housing has an output shaft geared to the needle. At least one control circuit energizes the motor to cause the output shaft of the motor to rotate, such as to oscillate.

In another aspect, a method includes advancing a needle supported by a telescoping housing into a working channel of an endoscope while the endoscope is not inside a patient. The method includes telescoping the housing to a first configuration until the needle protrudes from a distal end of the working channel, locking the housing in the first configuration, and removing the needle from the endoscope. The method then includes advancing the endoscope into an object to image a constituent of the object to be sampled. With the housing in the first configuration, the needle is advanced into the working channel until the needle protrudes from the distal end of the working channel. The method includes manipulating the housing to telescope the housing to urge the needle into the constituent of the object to be sampled, actuating a motor in the housing to rotate the needle, and engaging a syringe with a proximal part of the housing to withdraw from the needle harvested constituent for analysis.

In some embodiments, the EBUS device includes a biopsy needle having a main body extending between a proximal end and a distal end. The needle is configured to operably engage the motor, such that the motor can rotate the biopsy needle. A cutting tip located at the distal end and a central longitudinal axis extends between the proximal and distal ends. In addition, a hollow interior extends through the main body, such that the hollow interior of the needle is in fluidic communication with a tissue collector.

Some embodiments of the biopsy needle include a first cutting aperture disposed through the main body. In some embodiments, the first cutting aperture has a rectangular shape with a long end of the rectangular shape extending parallel to the central longitudinal axis of the biopsy needle. A second cutting aperture is also disposed through the main body. In some embodiments, the second cutting aperture has a rectangular shape identical to the first cutting aperture with a long end of the rectangular shape extending parallel to the central longitudinal axis of the biopsy needle. Each of the first and second cutting apertures creates a channel with a central axis extending from an exterior surface of an interior surface of the main body, and the central axes of the channels are aligned in some embodiments. Furthermore, the first and second cutting apertures are longitudinally spaced in a proximal direction from the distal end of the main body, such that there is a continuous portion of the main body between the first and second cutting apertures and the distal end of the main body. In some embodiments, the first and second cutting apertures are diametrically opposed from each other about the main body of the biopsy needle.

In some embodiments, each of the cutting apertures are defined by a boundary circumscribing the aperture and the boundary is generally flush with an exterior surface of the main body. In some embodiments, each cutting aperture includes a beveled channel wall extending between the interior and an exterior surface of the main body of the biopsy needle to direct tissue into the interior of the biopsy needle. In some embodiments, each of the cutting apertures includes an outwardly, laterally extending flange relative to the central longitudinal axis of the needle.

In some embodiments, each cutting aperture is the same distance from the distal end of the biopsy needle. In some embodiments, the first cutting aperture is longitudinally spaced from the second cutting aperture, such that the two cutting apertures are different distances from the distal end of the biopsy needle.

In some embodiments, a portion of the biopsy needle proximal to the of the cutting apertures includes a plurality of annular grooves circumscribing an exterior surface of the biopsy needle.

Some embodiments further include a third and a fourth cutting aperture disposed through the main body. The third cutting aperture has a rectangular shape with a long end of the rectangular shape extending parallel to the central longitudinal axis of the biopsy needle. The fourth cutting aperture has a rectangular shape identical to the first cutting aperture with a long end of the rectangular shape extending parallel to the central longitudinal axis of the biopsy needle. The third and fourth cutting apertures are longitudinally spaced in the proximal direction from the distal end of the main body, such that the continuous portion of the main body is between the third and fourth cutting apertures and the distal end of the main body. In addition, the third and fourth cutting apertures are diametrically opposed from each other about the main body of the biopsy needle and the third cutting aperture is circumferentially spaced from the first cutting aperture by generally 45 degrees.

Some embodiments further include a plurality of annular grooves proximate the cutting apertures. In some embodiments, the distal end of the biopsy needle includes a beveled tip.

The invention accordingly comprises the features of construction, combination of elements, and arrangement of parts that will be exemplified in the disclosure set forth hereinafter and the scope of the invention will be indicated in the claims.

The details of the present application, both as to its structure and operation, can best be understood in reference to the accompanying drawings, in which like reference numerals refer to like parts.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The phrases "in some embodiments," "according to some embodiments," "in the embodiments shown," "in other embodiments," and the like generally mean the particular feature, structure, or characteristic following the phrase is included in at least one implementation. In addition, such phrases do not necessarily refer to the same embodiments or different embodiments.

It is to be understood that principles of constructions and operation set forth in the above-incorporated U.S. patent documents apply to the disclosure herein in relevant part taking account of the features set forth herein.

Figure 1:
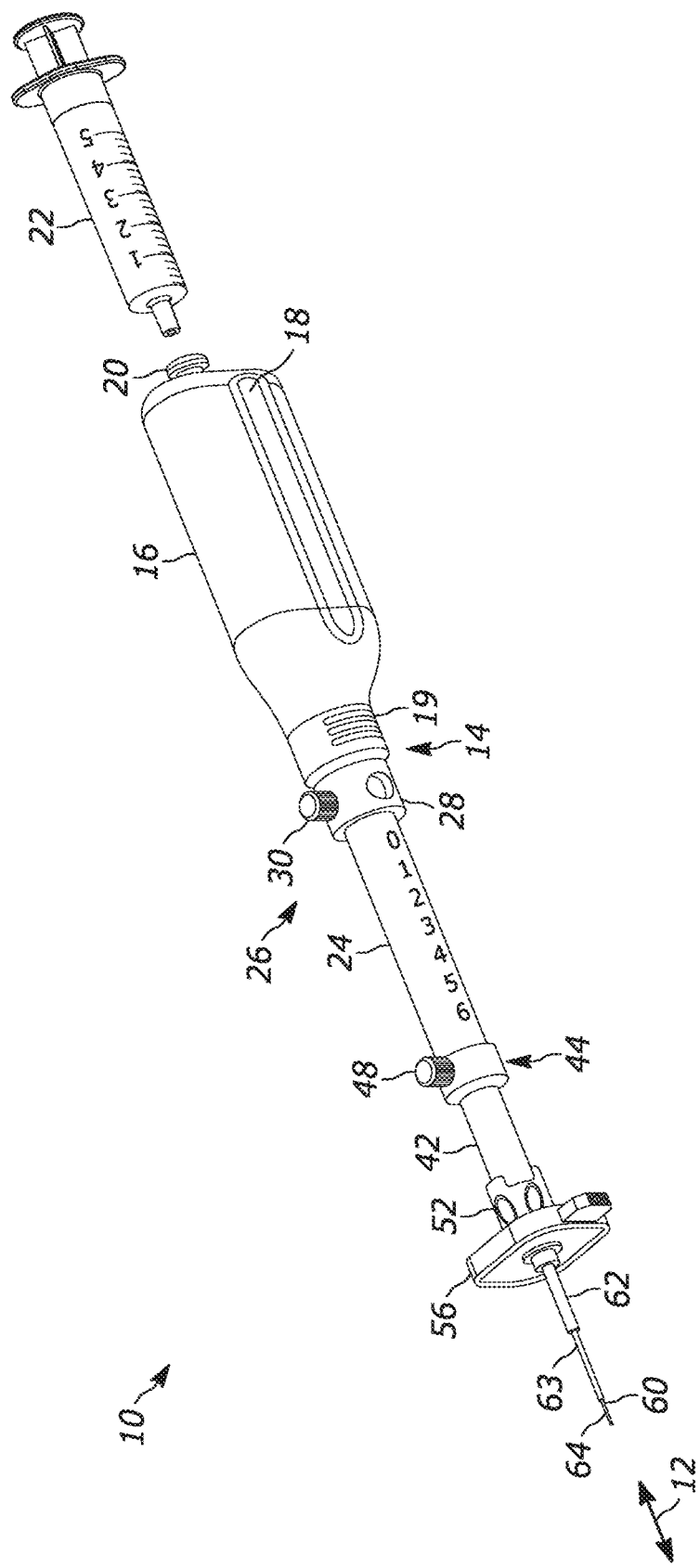
FIG. 1 is a perspective view of a first embodiment of a telescoping tissue harvesting assembly, showing a syringe in an exploded relationship with the assembly.

Referring to FIG. 1, an elongated telescoping assembly 10 is shown which defines a longitudinal axis 12 and which in the example shown can be configured as an endobronchial ultrasound needle (EBUS) assembly. The assembly 10 includes a housing 14 with at least two and in the example shown three segments that are telescopically engaged such that an inner segment nests inside and is slidably engaged with a middle segment which nests inside and is slidably engaged with an outer segment, with the segments having progressively smaller diameters from outer segment to inner segment.

In the example shown, these segments include a hollow handle segment 16 that is the proximal-most segment of the housing 14. The handle segment 16 may be formed in injection-molded plastic, like the remaining segments of the housing 14, and may have an ovular or oval transverse cross-section as shown to aid in gripping. Also, the handle segment 16 may include one or more longitudinally-oriented channel indentations 18 on its outer surface to promote gripping the raised circumferential ridges 19 on the distal portion of the handle segment 16 also to promote gripping. A connector fitting 20 such as a Luer fit may be provided near the proximal end of the housing segment 16 as shown to facilitate connection to external components such as a syringe 22. The fitting 20 may be hollow and may establish the proximal-most segment of a fluid channel that extends coaxially through the housing 14 and that will be described further in reference to FIG. 2.

Figure 2:
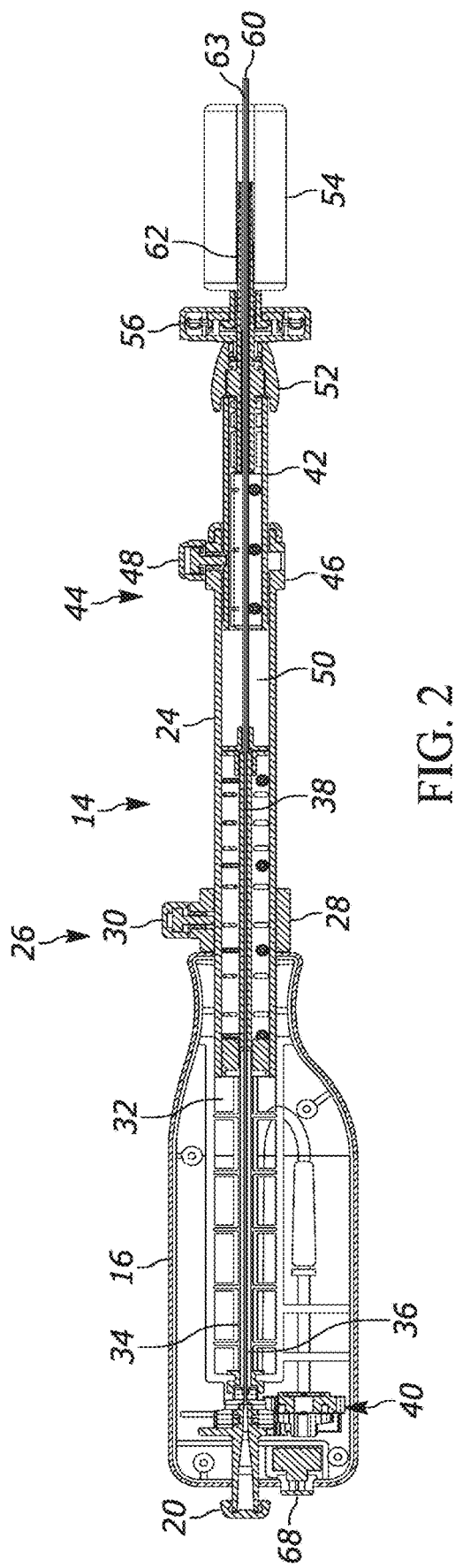
FIG. 2 is a side cut-away view of the assembly shown in FIG. 1 in an initial configuration outside the patient.
Figure 6:
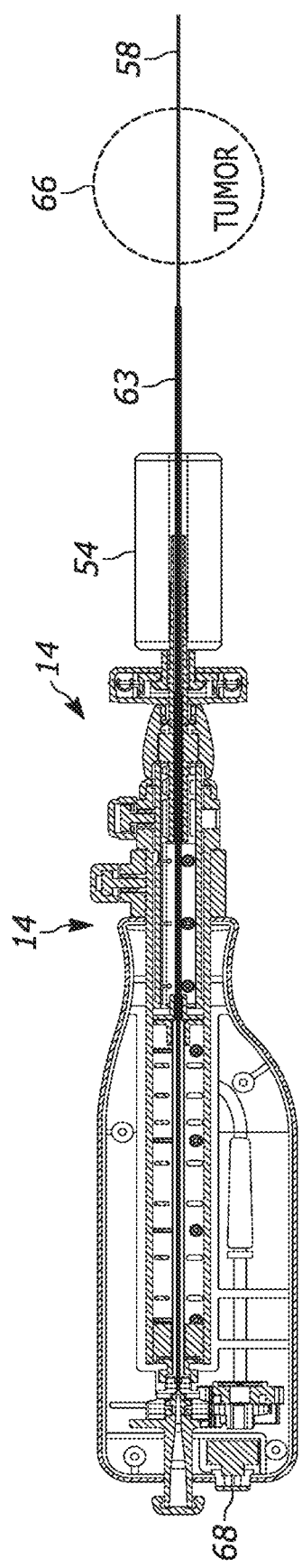
FIGS. 6 and 7 are a side cut-away views of the assembly shown in FIG. 1 in a configuration inside the patient to illustrate the necessity of the needle stop.

Indeed, and now cross-referencing FIGS. 1 and 2, a hollow, generally cylindrical middle segment 24 of the housing 14 extends distally away from the handle segment 16 and is slidably engaged with the handle segment 16 such that the middle segment 24 can telescope within the handle segment 16. To limit axial movement of the middle segment 24 within the handle segment 16, a manipulable mechanical outer stop 26 may be provided. In the example shown the outer stop 26 includes a cylindrical collar 28 that closely surrounds the middle segment 24 and a thumbscrew 30 extending transversely into the collar 28 and threadedly engaged therewith such that the thumbscrew 30 can be tightened against the middle segment 24 to hold the middle segment 24 stationary relative to the collar 28. The collar 28 in turn may be slidably engaged with the middle segment 24. When the stop 26 is set in the most distal position, the handle segment 16 is free to slide back and forth over the length of the middle segment 24. On the other hand, when the stop 26 is set in the most proximal position, the handle segment 16 cannot slide at all. As discussed further below, prior to inserting the needle, the user estimates the distance from the end of the sheath to the distal side of the tumor. The user then sets the stop 26 an appropriate length (the distance previously estimated) away from the distal end of the handle segment 16, tightening the thumbscrew at that position. This is done to limit the "throw" of the needle and prevent it from passing completely through the tumor as otherwise might occur as shown in FIG. 6 and mentioned further below.

The diameter of the middle segment 24 is marginally smaller than the diameter of a segment receiving void 32 formed coaxially in the handle segment 16 such that the middle segment 24 can reciprocate under hand pressure within the void 32.

Note that a central tube 34 forming a proximal portion 36 of the above-alluded to fluid channel can be provided in the handle segment 16 and received in or communicate with a central channel 38 of the middle segment 24, which central channel 38 also forms part of the above-mentioned fluid channel. The tube 34 prevents kinking of the needle within the void 32. In some embodiments the tube 34 may be omitted. The needle of the assembly, described further below, is coupled to a drive assembly 40 in the handle segment 16 through the proximal portion 36 of the fluid channel to impart oscillating rotational motion of the needle.

A hollow, generally cylindrical inner segment 42 of the housing 14 extends distally away from the middle segment 24 and is slidably engaged with the middle segment 24 such that the inner segment 42 can telescope within the middle segment 24. To prevent axial movement of the inner segment 42 within the middle segment 24, a manipulable mechanical inner stop 44 may be provided. In the example shown in FIG. 2, the inner stop 44 includes a cylindrical collar 46 that closely surrounds the inner segment 42 and a thumbscrew 48 extending transversely into the collar 42 and threadedly engaged therewith such that the thumbscrew 48 can be tightened against the inner segment 42 to hold the inner segment 42 stationary relative to the collar 46. The collar 46 in turn may be made integrally with or adhered to by solvent bonding, rf sealing, or other technique to the middle segment 24. The diameter of the inner segment 42 is marginally smaller than the diameter of a segment receiving void 50 formed coaxially in the middle segment 24 such that the inner segment 42 can reciprocate under hand pressure within the void 50 when the thumbscrew 48 is not tightened against the inner segment 42.

A hollow coupling 52 is attached to or formed integrally on the distal end of the inner segment 42 to couple the housing 14 with an endoscope 54. The coupling 52 may be formed, e.g., with interior Luer threads that can directly engage a Luer fitting on the endoscope 54 or that can engage an adapter 56 that in turn is configured to engage the endoscope 54 that does not have a Luer-like connector. An example adapter 56 is shown in FIGS. 13-16 and described further below.

At least one hollow needle 58 having one or more hollow needle segments is supported by the housing 14. The needle 58 extends from a distal cutting tip 60 through the inner, middle, and handle segments 42, 24, 16 to the drive assembly 40, which as further disclosed below includes at least one motor with an output shaft geared to the needle 58. When the housing 14 is coupled to the endoscope 54, the needle 58 extends through the working channel of the endoscope. A coupler tube 62 can extend distally beyond the distal segment 42 as shown and is effectively an extension of the distal segment 42 that provides structural integrity between the distal segment 42, the Luer connector 52, the adapter 56 (if applicable), and the endoscope.

Figure 17:
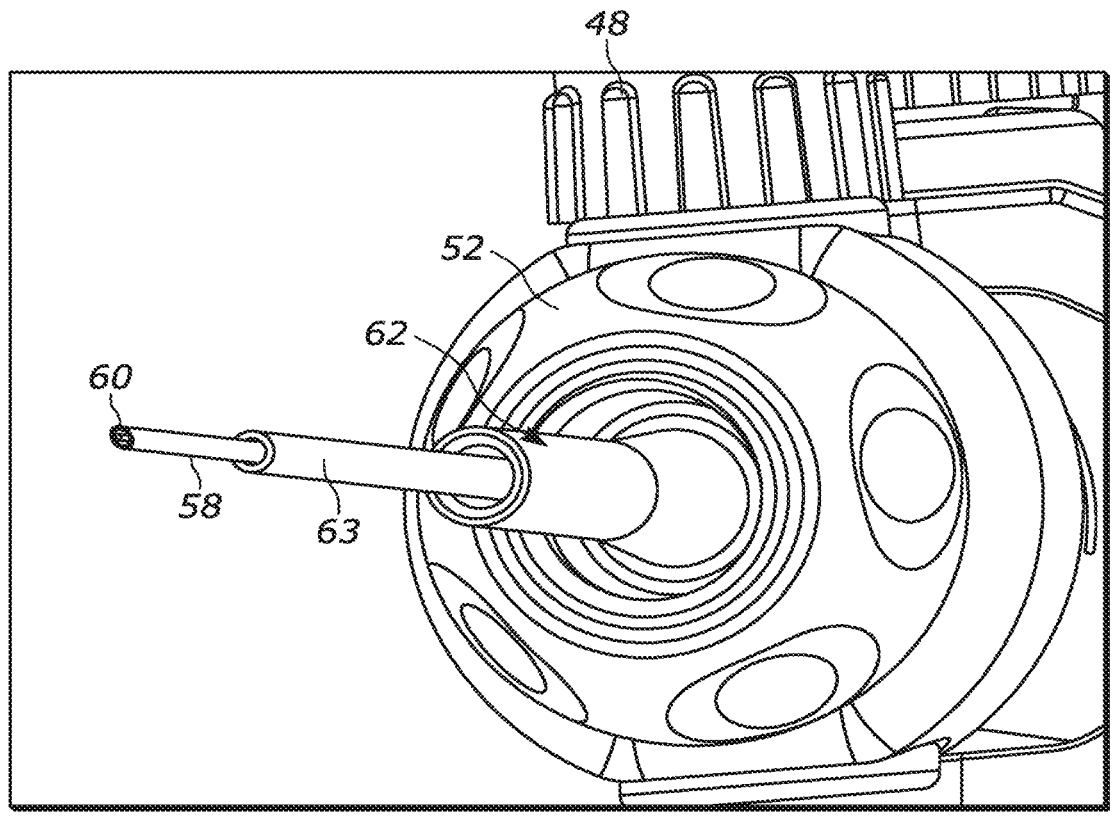
FIG. 17 is an isometric view of the distal portion of the assembly shown in FIG. 1.
Figure 18:
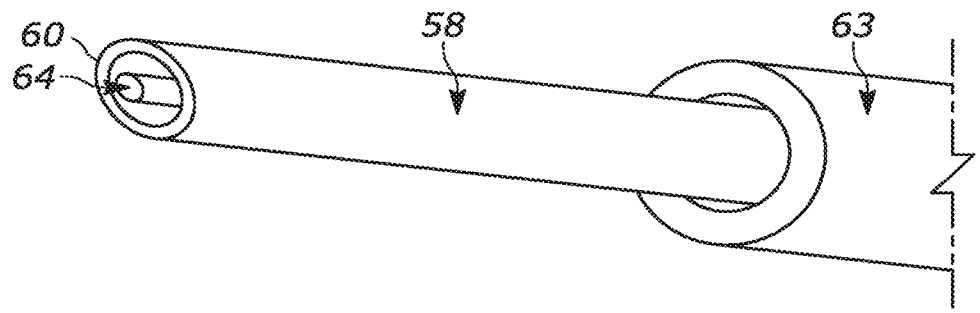
FIG. 18 is a detail view of the distal needle components of FIG. 17.
Figure 19:
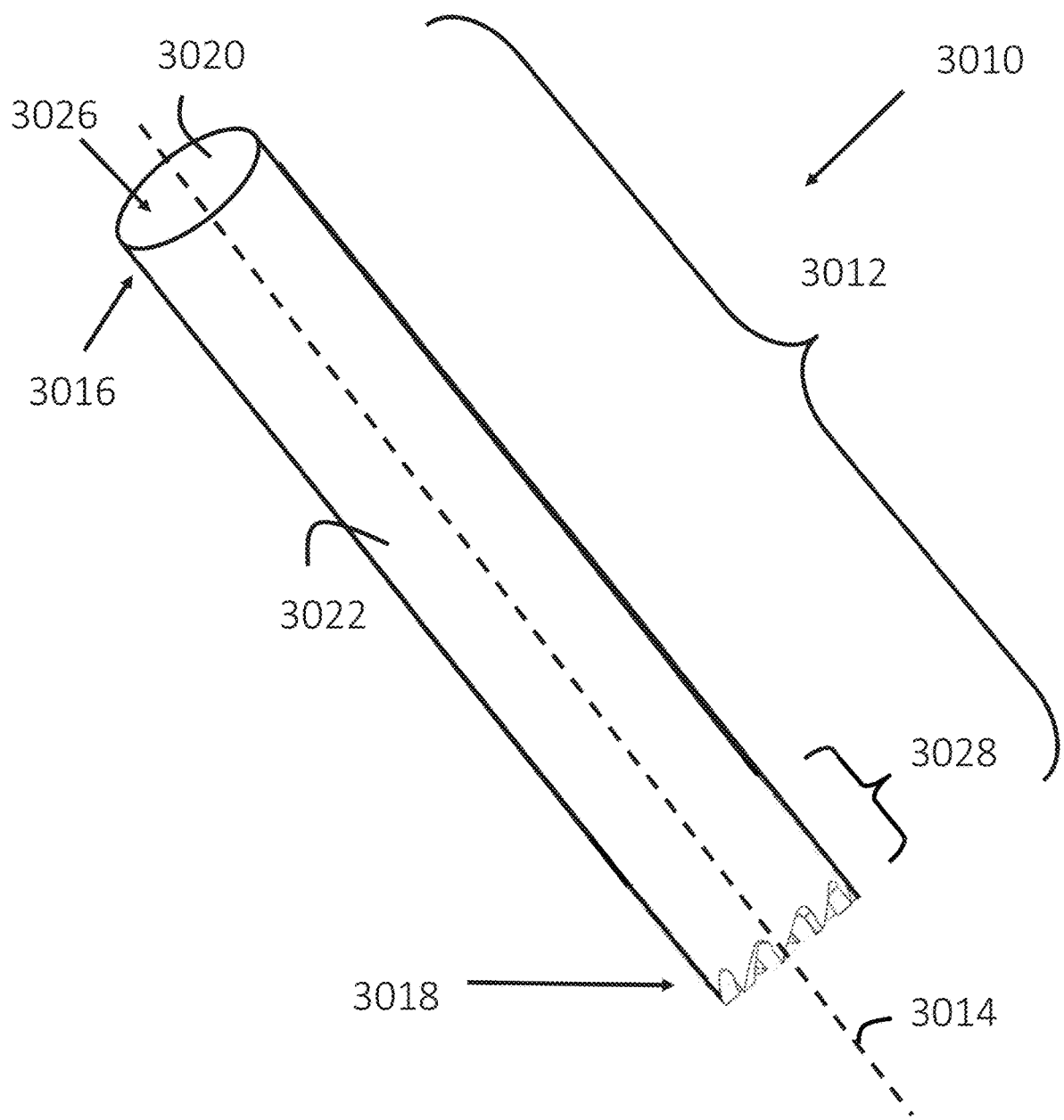
FIG. 19 is a perspective view of an embodiment of a biopsy needle used for the collection of cellular materials within a biopsy area.

The interior channel of the hollow needle 58 forms all or part of the above-mentioned fluid channel. Refer briefly to FIGS. 17 and 18. A sheath 63 closely surrounds the needle 58, and a stylet 64 (FIG. 18) can extend through the fluid channel and out of the distal end 60 of the needle for sliding in and out of the needle as needed, e.g., to impede epithelial tissue from entering the needle prior to biopsy of tumor tissue.

Figure 3:
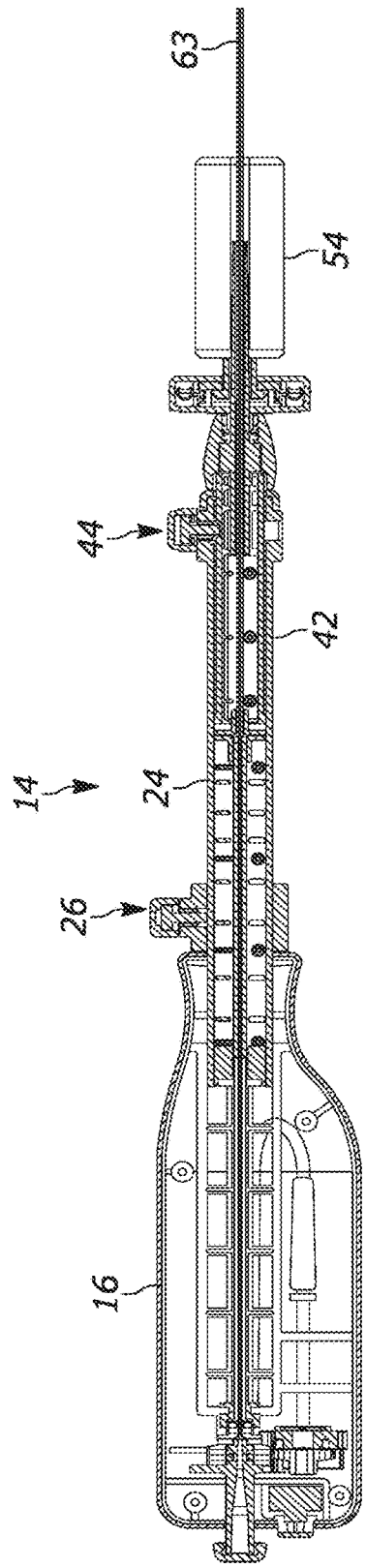
FIGS. 3 and 4 are a side cut-away views of the assembly shown in FIG. 1 in a configuration outside the patient in which the assembly is adjusted telescopically to establish a length of protrusion of the needle distally beyond the endoscope.
Figure 4:
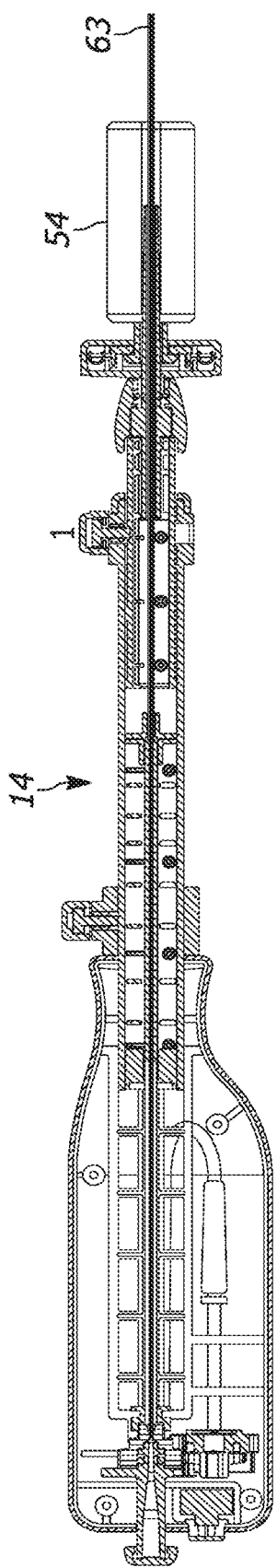

In FIG. 2, the housing 14 is engaged with the endoscope 54 prior to advancing the endoscope into an object such as a patient's body. The inner segment 42 has been moved relative to the middle segment 24 such that the tip of the needle and the distal portions of the sheath 62 and stylet 64 extend marginally out of the distal end of the working channel of the endoscope, and then the mechanical stop 44 manipulated to lock the housing segments axially to prevent further telescoping movement. FIG. 2 shows the initial, fully-extended configuration; FIGS. 3 and 4 show the device after the distal segment 42 has been moved relative to the middle segment 24.

When this configuration of the housing 14 has been established, the housing 14 is disconnected from the endoscope and the endoscope then advanced into the patient. The housing 14 then may be re-connected to the endoscope in the configuration shown in FIG. 4.

Figure 5:
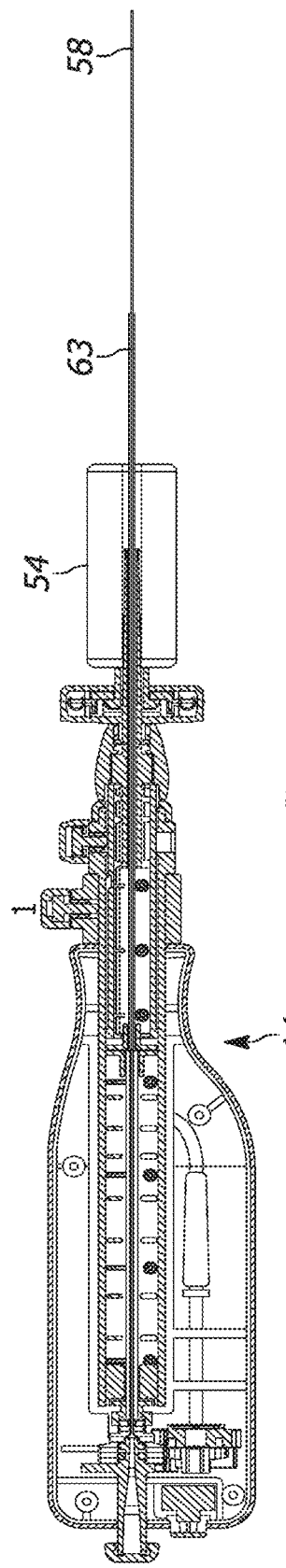
FIG. 5 is a side cut-away view of the assembly shown in FIG. 1 in a shortened configuration to project the needle distally beyond the endoscope.
Figure 7:
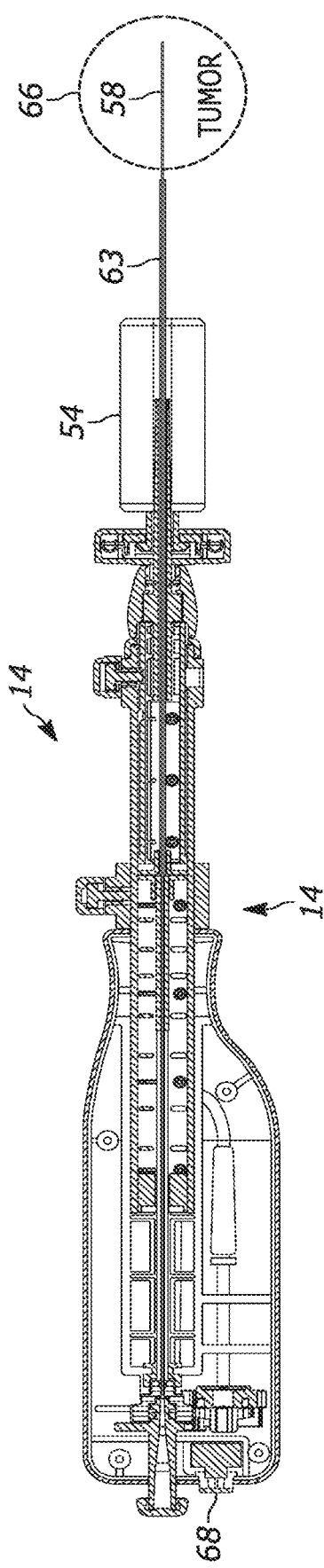
Figure 8:
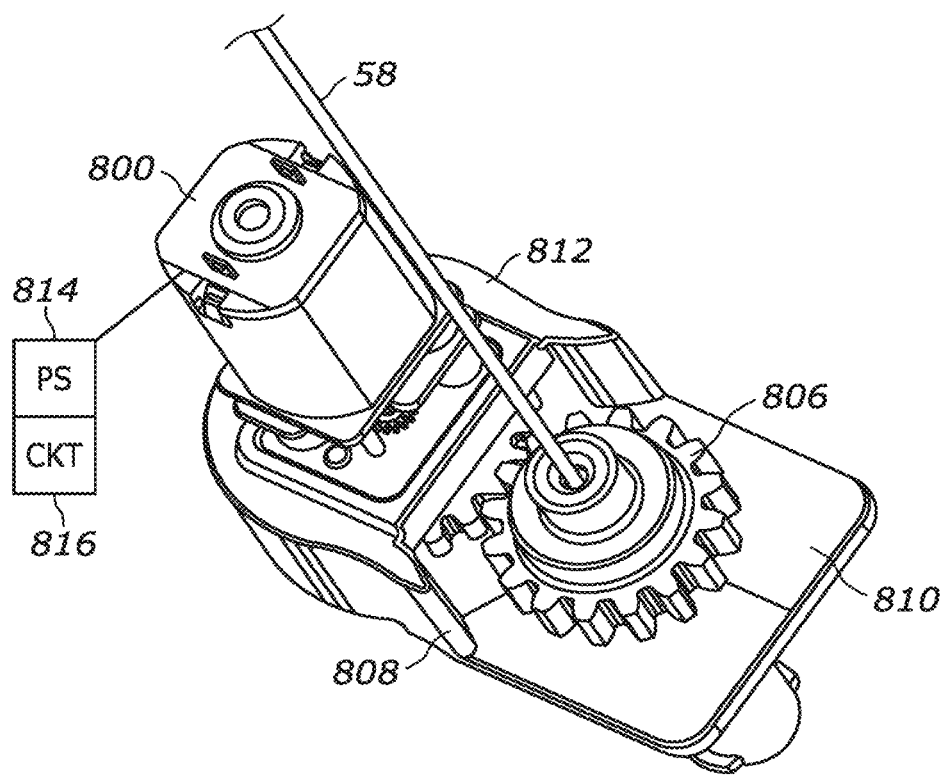
FIGS. 8 and 9 are isometric views from two different perspectives of the motor, gear, and needle subassembly.
Figure 9:
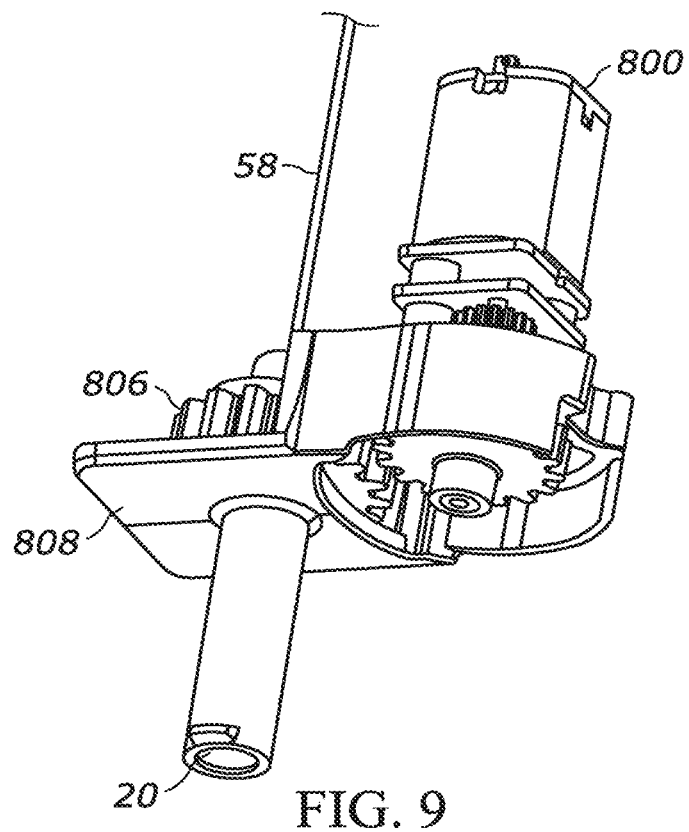
Figure 10:
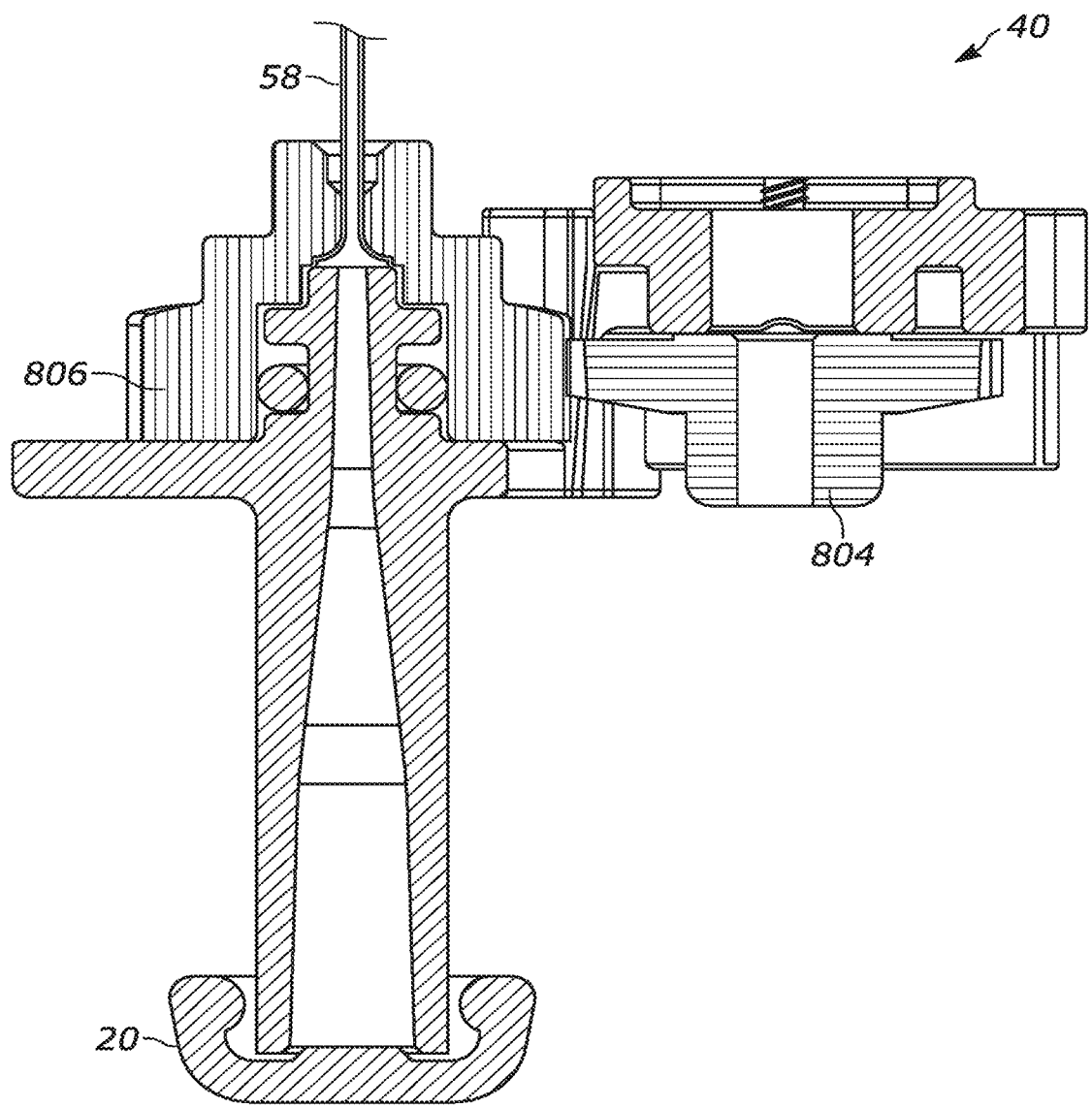
FIG. 10 is a side cut-away view of the subassembly shown in FIGS. 8 and 9.

FIGS. 5-7 illustrate that subsequently, a shorter configuration of the housing 14 can be established by unlocking the proximal stop 26 and moving the handle and middle segments 16, 24 relative to each other to cause the needle 58 to protrude further distally away from the distal end of the endoscope 54 and the distal end of the needle 58 out of the distal end of the sheath 62. The stop 26 can be manipulated to limit the position of the needle relative to the endoscope to avoid over-extending the needle into the patient. In this way, the needle 58 can penetrate tissue 66 (FIG. 7) such as a tumor to be sampled without unintentionally overextending the needle (FIG. 6). The drive assembly 40 can be actuated by manipulating an actuator such as button 68 (FIGS. 2 and 7) on the housing 14 to energize, via a control circuit, a motor to cause the output shaft of the motor to oscillate. As disclosed further below, the output shaft is geared to the needle to cause the needle to rotate in one direction or oscillate in two directions (alternating between clockwise and counterclockwise) in the tissue 66, drawing portions of the tissue in the needle. The syringe 22 shown in FIG. 1 can be engaged with the housing 14 to evacuate the interior of the needle to harvest the tissue for analysis.

Figure 11:
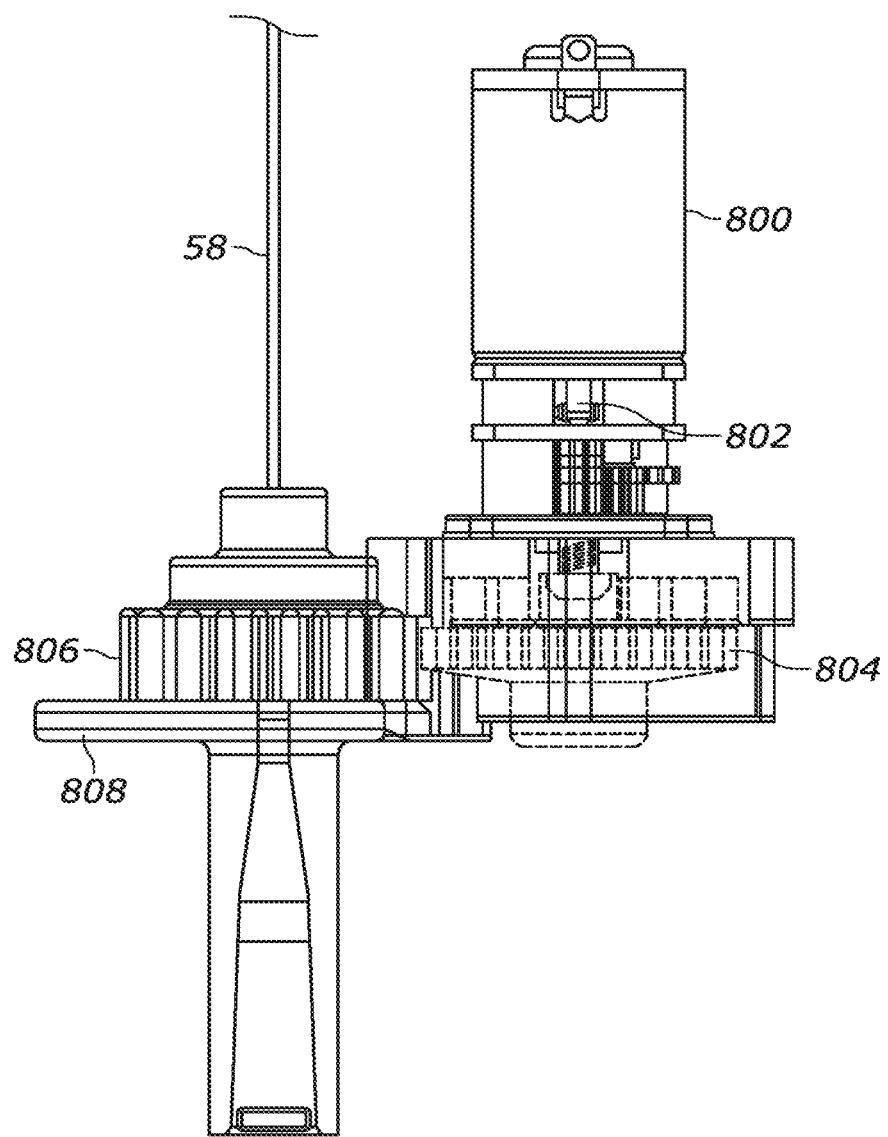
FIG. 11 is a side view, partially transparent, of the subassembly shown in FIGS. 8 and 9.

FIGS. 8-11 illustrate that an example embodiment of the drive assembly 40 in the handle segment 16 may include one or more electric motors 800 (in the example shown, only one motor) coupled to the needle 58 through one or more gears such as but not limited to spur gears. In the example shown and as best illustrated in FIG. 11, an output shaft 802 of the motor 800 is coupled to one or more motor gears 804 that are meshed with one or more needle gears 806, with the needle 58 being bonded to or molded with or otherwise affixed to the needle gears 806 to rotate with the needle gears 806. The gear train may be configured to reduce rotational speed from the speed of rotation of the motor shaft 802 to a slower needle rotation speed.

The motor 800 with gears can be supported on a motor plate assembly 808, which may include two flat plates 810, 812 (FIG. 8) that are parallel to each other and that are staggered in the longitudinal dimension from each other to respectively support the needle gear 806 with needle 58 and the motor 800 with motor gear 804. As shown schematically in FIG. 8, a power supply 814 (such as a battery) is disposed in the housing 14 and is connected to the motor 800 to energize the motor 800.

Also, a control circuit 816 is located in the housing 14 and is coupled to the button 68, so that when the button 68 is manipulated, the control circuit is activated to energize the motor 800 to cause the output shaft 802 of the motor (and, hence, the needle 58) to rotate in a single direction only (i.e., clockwise or counterclockwise) or to oscillate (i.e., to rotate alternatingly between CW and CCW). For oscillation, the control circuit alternatingly reverses the direction of rotation of the motor shaft, from clockwise to counter-clockwise and back again, based on a time period for rotation in one direction or a position of rotation. Any of the control circuits described in the above-referenced U.S. patent may be used for this purpose. Note that for single direction rotation only, no control circuit need be used other than an electrical connection from a battery to the switch that energizes the motor.

Figure 12:
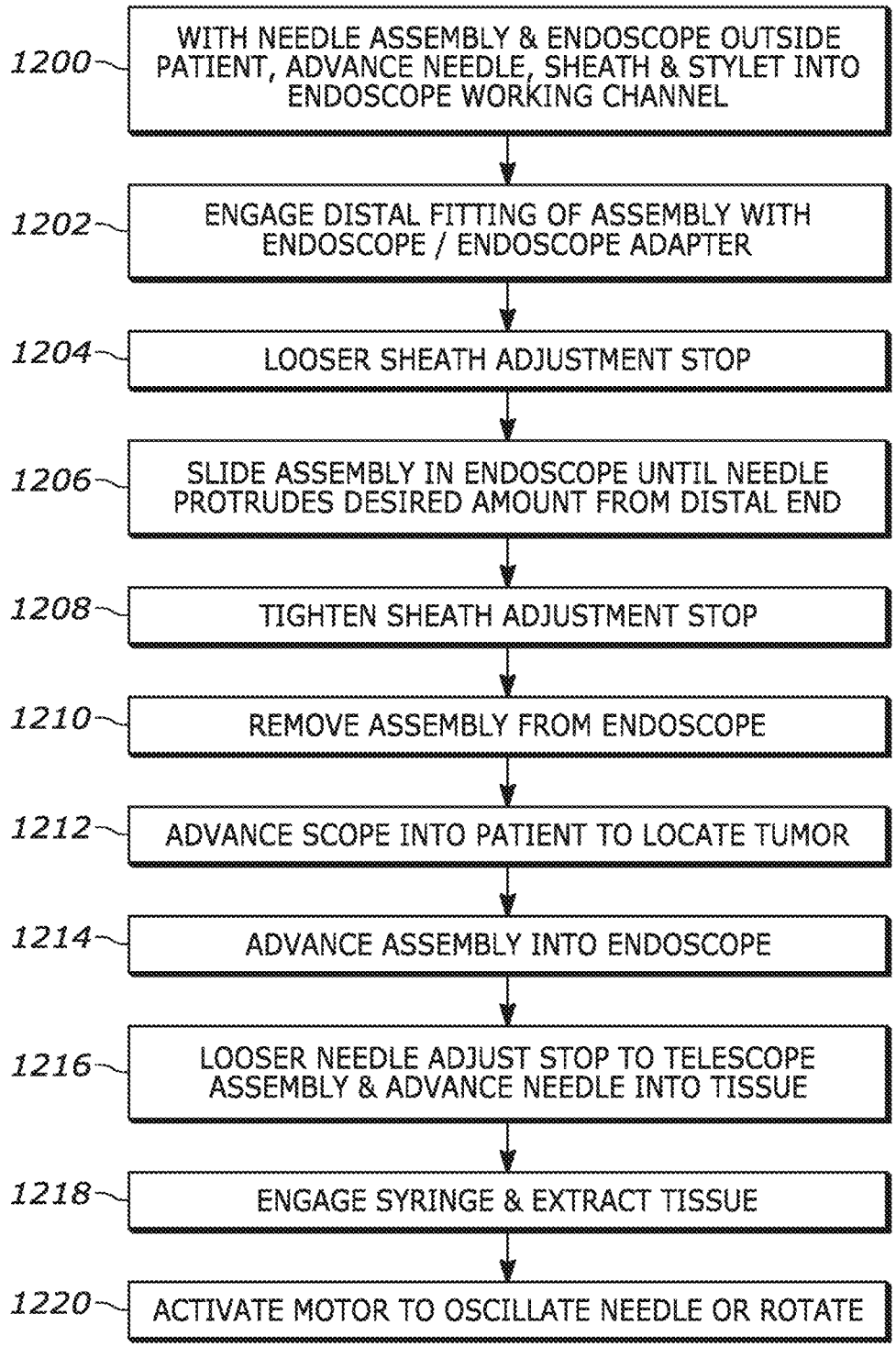
FIG. 12 is a flow chart of the use steps of the assembly shown in FIG. 1.

FIG. 12 illustrates a method of using the assembly 10 shown in FIGS. 1-11 with the endoscope 54. Commencing at block 1200, with the assembly 10 and endoscope outside of the patient, the needle (with sheath and typically stylet) is engaged with the endoscope working channel. At block 1202 the coupling 52 is coupled to the endoscope or, when needed, the adapter 56 which in turn is coupled to the endoscope. Moving to block 1204, the stop 44 is loosened and at block 1206 the assembly 10 is moved until the needle, sheath, and stylet protrude from the distal end of the endoscope by a desired amount. Proceeding to block 1208, the stop is tightened to lock the configuration of the housing 14 of the assembly 10 in place and the assembly 10 removed from the endoscope at block 1210.

When it is desired to harvest tissue from a patient, at block 1212 the endoscope is advanced into the patient under visualization to locate the tissue to be harvested, e.g., a tumor. The assembly 10 is advanced into the endoscope working channel at block 1214 so that the needle, sheath, and stylet protrude (the distance set in step 1206) beyond the distal tip of the endoscope, at which point the stop 26 can be loosened at block 1216 to telescope the housing 14 as needed to advance the needle into the tissue. Once the needle 58 is in the tumor, the stylet 64 is removed and the syringe 22 is attached to the fluid channel previously occupied by the stylet. Suction is applied by the syringe at block 1218, and then the motor is activated at block 1220 by manipulating the button 68 to rotate or oscillate the needle within the needle to harvest tissue, which can be evacuated at block 1220.

Figure 13:
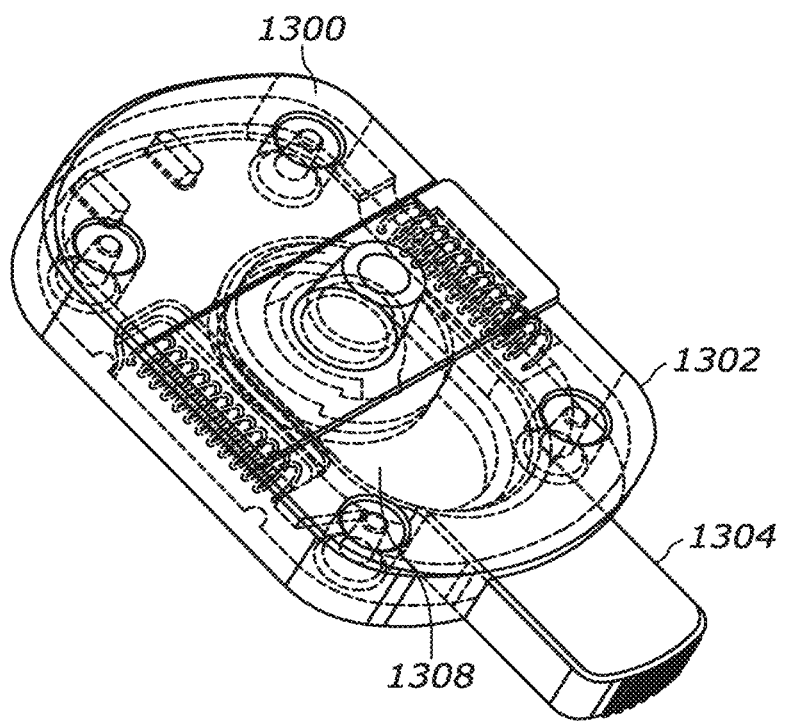
FIG. 13 is a partially transparent perspective view of an example assembly-to-endoscope adapter.
Figure 14:
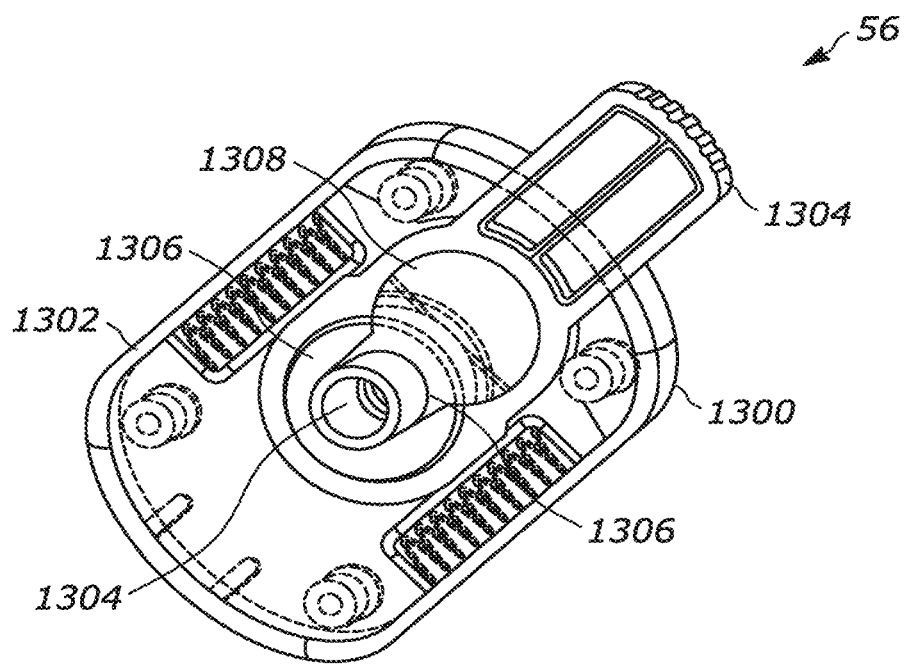
FIG. 14 is a bottom partially transparent view of the adapter shown in FIG. 13.
Figure 15:
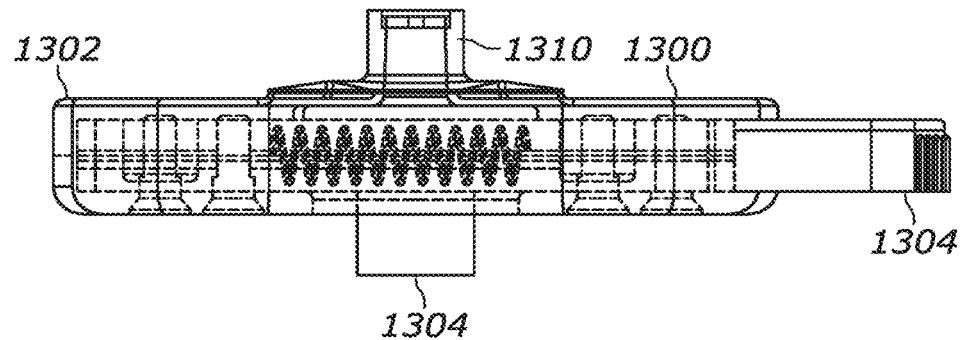
FIG. 15 is a side partially transparent view of the adapter shown in FIG. 13.

As understood herein, some endoscopes have fittings that can be engaged with the coupling 52 shown in FIG. 1. Other endoscopes may have couplings such as the mushroom-shaped hollow coupling 1600 shown in FIG. 16 that cannot engage the coupling 52 of the needle assembly, in which case the adapter 56 is provided. FIGS. 13-15 illustrate an example adapter 56.

Figure 16:
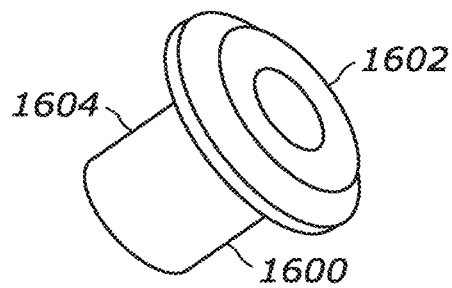
FIG. 16 is an isometric view of the working channel collar of an example endoscope.

The adapter 56 includes a flat hollow body 1302 with a hollow receptacle 1304 through which the head 1602 of the coupling 1600 of the endoscope 54 in FIG. 16 can be received. As shown, the head 1602 has a larger diameter than a stalk 1604 of the coupling 1600 and the head 1602 may have a beveled outer edge, giving the endoscope coupling 1600 a somewhat mushroom-shaped appearance.

A slide 1304 is slidably disposed in the body 1302 of the adapter 1300. The slide 1302 is formed with a small opening 1306 and a large opening 1308, with a passageway between the openings. The small opening 1306 and passageway to the large opening is smaller than the diameter of the head 1602 of the coupling 1600 of the endoscope, whereas the large opening 1308 has a diameter larger than the diameter of the head 1602.

The slide 1304 may be spring-loaded into the configuration shown in FIGS. 13 and 14, in which the small opening 1306 is substantially aligned (coaxially) with the receptacle 1304. The slide 1304 can be pushed inwardly toward the body 1302 of the adapter 1300 against spring pressure to align the large opening 1308 coaxially with the receptacle 1304, allowing the head 1602 to be advanced through the receptacle 1304 and large opening 1308. The slide may then be released to cause it to move outward as the passageway between the openings 1306, 1308 rides past the stalk 1604 of the coupling 1600 until the small opening 1306 is once again aligned with the receptacle 1304, trapping the head 1602 of the coupling within the adapter 1300 to thereby engage the adapter with the coupling 1600. Opposite the receptacle 1304, the adapter 1300 is formed with a fitting 1310 such as a Luer fitting configured to engage the coupling 52 of the needle assembly 10, thereby coupling the needle assembly 10 with the endoscope 54. Both the fitting 1310, body 1302, and receptacle 1304 of the adapter 1300, as well as the coupling 1600 of the endoscope, are hollow such that the needle 58 (and coupler tube 62, sheath 63, and stylet 64) can extend completely through the coupling structure. To decouple the endoscope 54 from the needle assembly 10, the slide 1304 is once again squeezed inwardly to align the large opening 1308 with the receptacle 1403, allowing the head 1602 of the endoscope coupling to be withdrawn from the adapter 1300.

Accordingly, an adapter for connecting a needle assembly to an endoscope includes one or more of the following components: a body formed with a hollow receptacle through which a head of an endoscope coupling of the endoscope can be received. The head has a larger diameter than a stalk of the endoscope coupling. A slide is slidably disposed in the body and is formed with a small opening, a large opening, and a passageway between the openings. The diameter of the small opening and the diameter of the passageway are smaller than the diameter of the head and larger than the diameter of the stalk, whereas the diameter of the large opening is diameter larger than the diameter of the head. The slide is movable from a first configuration, in which the small opening is substantially aligned (coaxially) with the receptacle, and a second configuration, in which the large opening is aligned coaxially with the receptacle, allowing the head to be advanced through the receptacle and large opening. The slide may then be moved back to the first configuration, trapping the head of the coupling within the adapter.

Some embodiments of the present invention include a biopsy needle that dramatically increases cellular material (i.e., cells) yield per pass. By collecting more cellular material per pass, the biopsy procedure requires fewer passes and is completed in shorter periods of time over conventional biopsy needles.

Referring now to FIGS. 19-33, biopsy needle 3010 is configured to penetrate one or more layers of tissues to obtain a sample of cellular material (such as cells or fluids) from within a target biopsy area. The cellular material is then analyzed to diagnose a medical condition or to rule out a disease. Biopsy needle 3010 is typically constructed of medical grade stainless nitinol, steel, or carbon steel; however, it is appreciated that biopsy needle 3010 may be constructed from other metals, polymers, carbon fiber, plastics, resins, composites, or any other biocompatible materials, which are pharmacologically inert.

Generally, biopsy needle 3010 comprises elongated shaft 3012 extending along central longitudinal axis 3014 from proximal end 3016 to distal end 3018. Elongated shaft 3012 includes internal surface 3020, external surface 3022, and body 3024 extending between internal surface 3020 and external surface 3022 of elongated shaft 3012. Moreover, internal surface 3020 of elongated shaft 3012 defines bore 3026, such that elongated shaft 3012 is hollow to facilitate the collection of cellular material from within the biopsy area.

Specifically, upon insertion of biopsy needle 3010 within a patient, the biopsy needle is manipulated (e.g., rotated and/or translated about its central longitudinal axis 3014) to enable the collection of cellular material and fluid. Once the cellular material is dislodged via the manipulation of biopsy needle 3010, the cellular material flows within bore 3026 from distal end 3018 to proximal end 3016 of biopsy needle 3010 and is collected within a collection reservoir (e.g., syringe or other devices) in mechanical communication with proximal end 3016 of biopsy needle 3010. Furthermore, distal end 3018 of biopsy needle 3010 includes retrieval section 3028 configured to scrape, tear, bump, grind, cut, sheer, hammer, or slash portions of intact cellular material located within the biopsy area to facilitate their collection within the collection reservoir through bore 3026.

Figure 20A:
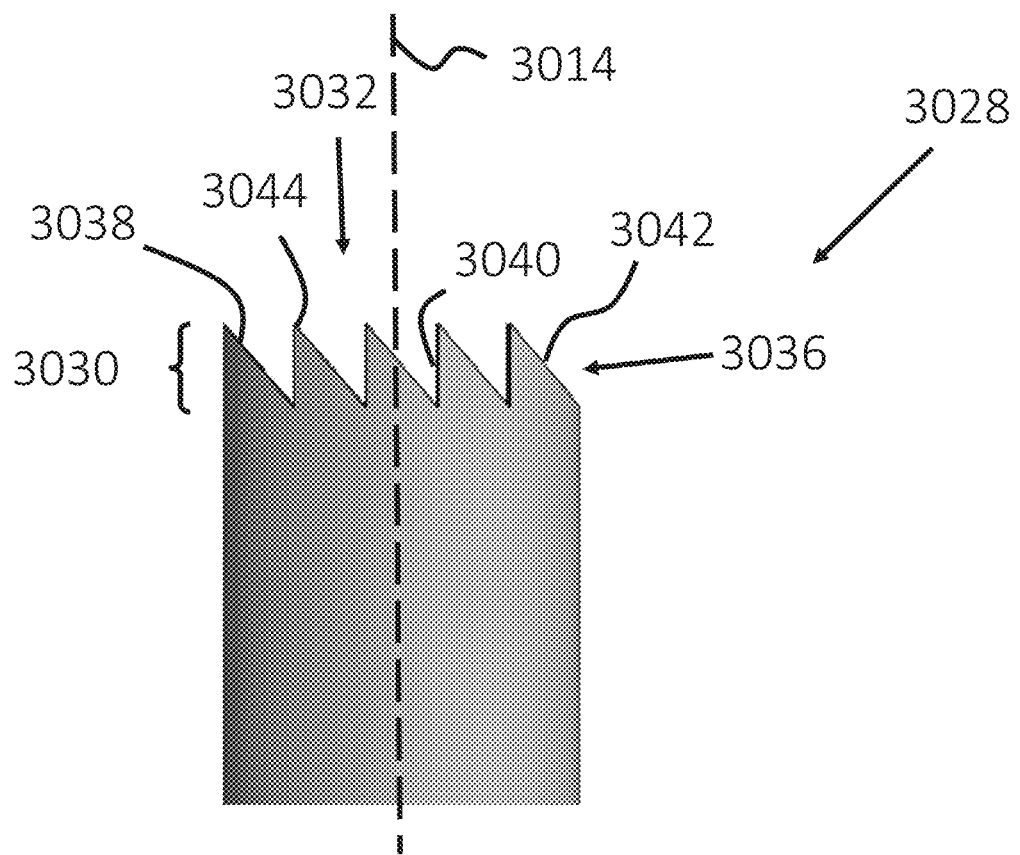
FIG. 20A is a side view of an embodiment of a retrieval section of a biopsy needle used to collect cellular materials with a first and second tooth design.
Figure 20B:
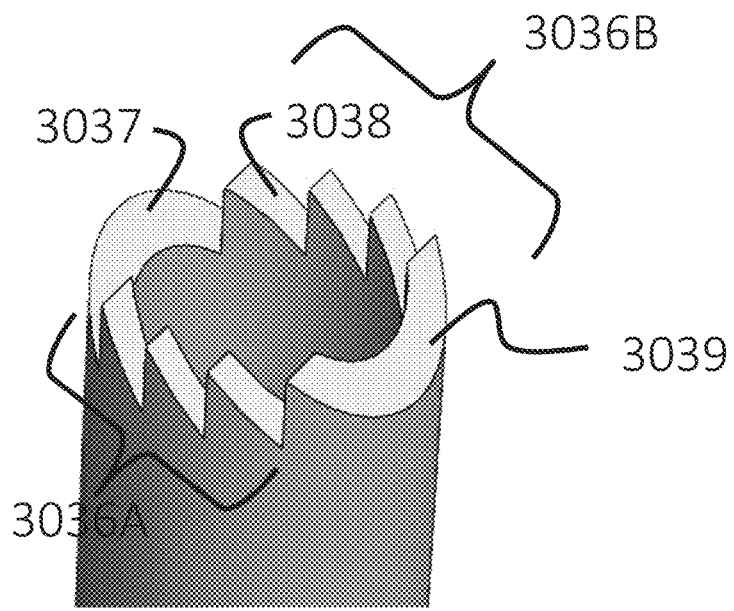
FIG. 20B is a perspective view of an embodiment of a retrieval section of a biopsy needle used to collect cellular materials with a first and second tooth design.

FIGS. 20A and 20B depict an embodiment of retrieval section 3028 disposed at distal end 3018 of biopsy needle 3010. As shown, retrieval section 3028 includes cutting edge 3030 disposed at leading-edge 3032 of retrieval section 3028. Cutting edge 3030 operably engages with the surrounding tissues to sheer off and dislodge cellular material from within the biopsy area during the biopsy procedure. In such embodiments, cutting edge 3030 includes alternating cutting designs disposed about a circumference of retrieval section 3028. In particular, a first cutting design and a second cutting design alternate to provide for the efficient capture of large portions of intact cellular material from within the biopsy area.

Cutting edge 3030 includes a first cutting design having a plurality of teeth 3036. Each tooth 3038 comprises face 3040, back 3042, and point 3044. A neutral rake angle of 0 degrees (i.e., rake angle being perpendicular to the direction of cut) is shown. The rake angle determines the angle of the cutting face 3040 of each tooth 3038. Moreover, having a rake angle of 0 degrees results in a vertical tooth 3038 that cuts faster and more aggressively. Furthermore, each tooth 3038 of cutting edge 3030 has a fleam angle (or bevel angle) of 0 degrees. In particular, the fleam is the angle across face 3040 of tooth 3038. The fleam permits each tooth 3038 to perform a tip-cut action—chiseling off cellular material as biopsy needle 3010 is manipulated and rotated about central longitudinal axis 3014.

In some embodiments, as depicted in FIG. 20B, cutting edge 3030 includes a single elongated tooth 3039, extending about leading-edge 3032 of retrieval section 3028 between groups of diametrically opposed teeth. Each tooth in groups 3036A and 3036B are longitudinally spaced in a distal direction moving from tooth 3039 to seat 3037, which is generally located in a diametrically opposed relation to tooth 3039. The rake and fleam angles of tooth 3039 and or the teeth in first plurality of teeth 3036A and second plurality of teeth 3036B may be the same or similar to those disclosed in relation to teeth depicted in FIG. 20A.

Figure 21A:
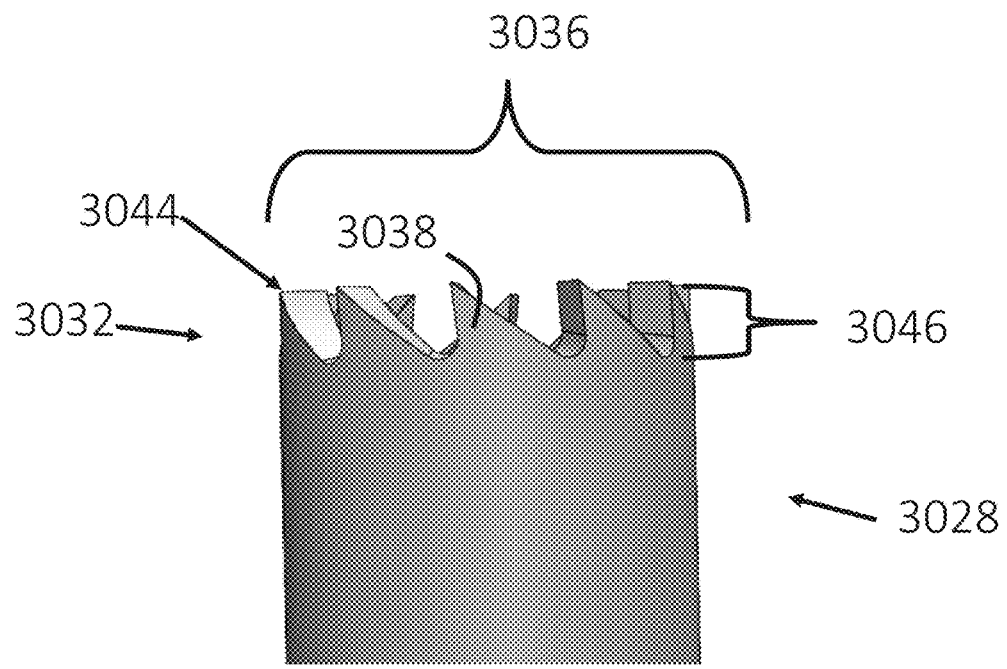
FIG. 21A is a side view of an embodiment of a retrieval section of a biopsy needle used to collect cellular material with a uniform tooth design.
Figure 21B:
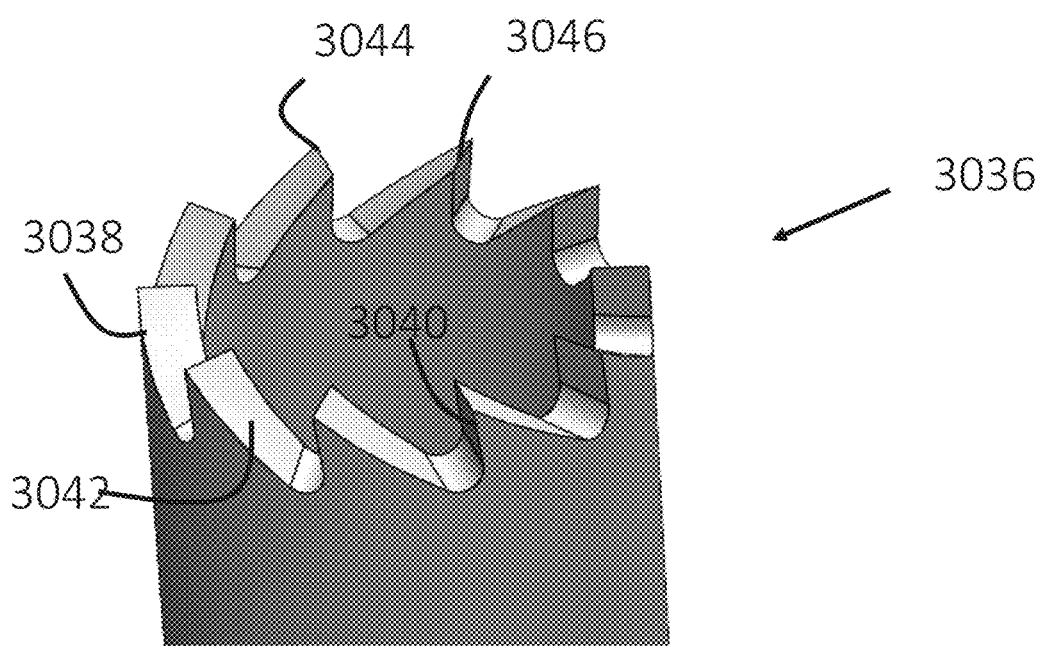
FIG. 21B is a perspective view of an embodiment of a retrieval section of a biopsy needle used to collect cellular material with a uniform tooth design.

FIGS. 21A and 21B depict an embodiment of retrieval section 3028 having a plurality of teeth 3036 circumferentially disposed about leading-edge 3032 of retrieval section 3028. Each tooth 3038 includes a distinct cutting design form the embodiments depicted in the previous figures. Each tooth 3038 includes face 3040, back 3042, and point 3044, each tooth 3038 of the third cutting design has an aggressive angle of attack due to the positive rake angle. Furthermore, the gullet depth 3046 (the space between point and the valley of each tooth) and gullet area is increased by the positive angle of attach thereby increasing the amount of cellular material that can be retrieved while cutting.

Figure 22A:
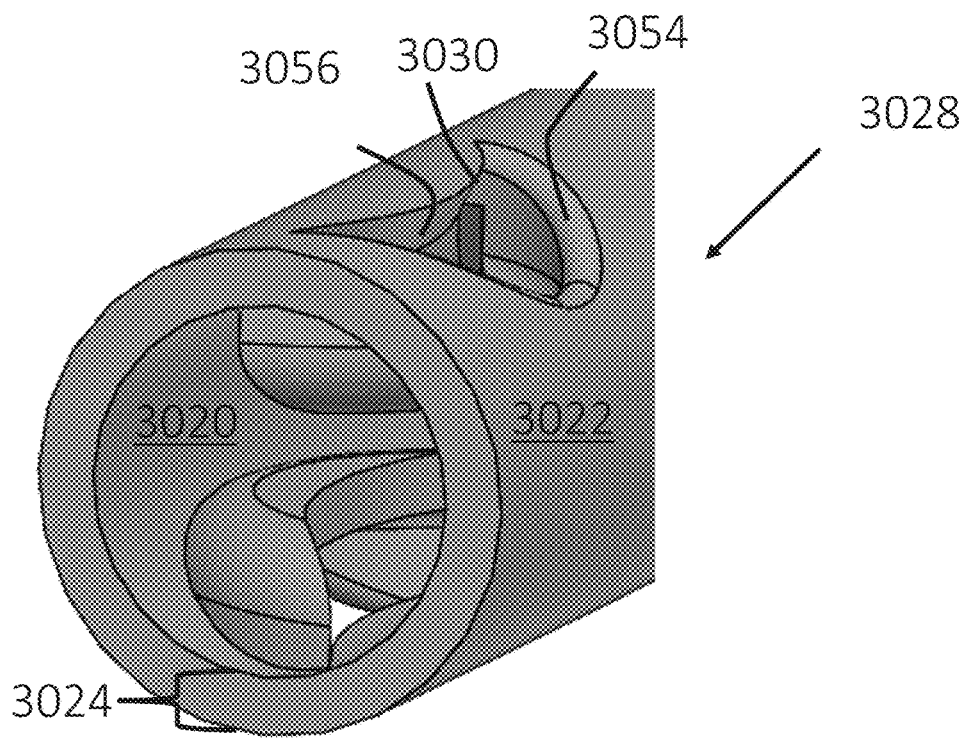
FIG. 22A is a cross-sectional view of an embodiment of a retrieval section of a biopsy needle used to collect cellular material having a plurality of cutting apertures disposed within the body of the elongated shaft.
Figure 22B:
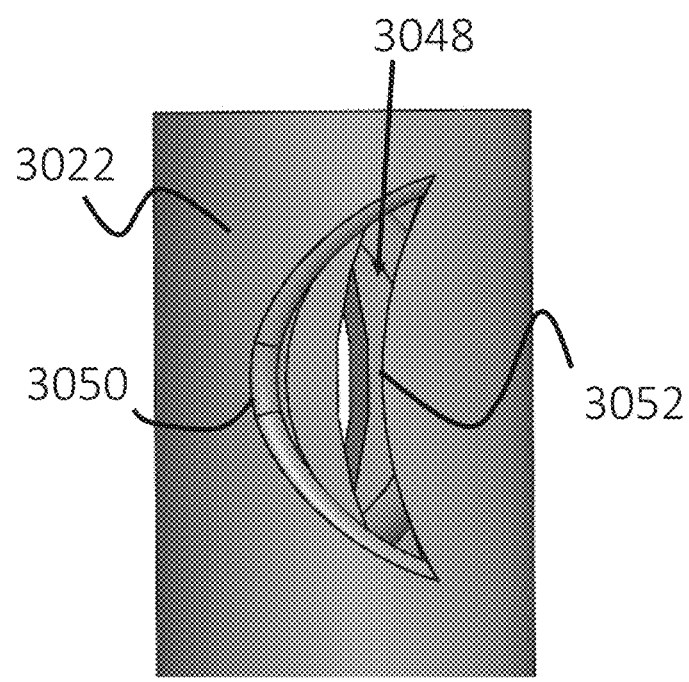
FIG. 22B is a close-up view of an embodiment of a cutting aperture disposed within the body of the elongated shaft.

FIGS. 22A and 22B depict another embodiment of retrieval section 3028. It should be noted that FIG. 22 do not depict the terminal end of biopsy needle 3010, which may have an angled or beveled shape to aid in the insertion of the needle and the cutting of tissue.

The embodiment of retrieval section 3028 as provided in FIG. 22 includes a plurality of crescent-shaped cutting apertures 3048 disposed through lateral wall/body 3024. Each cutting aperture 3048 includes major aperture edge 3050 (the edge with the longer length) and minor aperture edge 3052 (the edge with the shorter length). In particular, major aperture edge 3050 comprises aperture wall 3054 extending between internal surface 3020 and exterior surface 3022 of elongated shaft 3012. Specifically, major aperture edge 3050 has a semi-circular shaped edge; however, alternative embodiments are contemplated having various geometrically shaped edges, such as square, linear, and triangular. Similarly, minor aperture edge 3052 includes beveled wall 3056 extending between internal surface 3020 and external surface 3022. However, alternative embodiments are contemplated having various geometrically shaped edges, such as square, linear, and triangular.

Cutting edge 3030 of beveled wall 3056 is formed at the intersection of external surface 3022 and wall 3056. In some embodiments, a line intersecting the midpoints of both major aperture edge 3050 and minor aperture edge 3052 is aligned perpendicular to central longitudinal axis 3014 of needle 3010. In some embodiments, the line intersecting the midpoints of both major aperture edge 3050 and minor aperture edge 3052 is non-parallel to central longitudinal axis 3014 of needle 3010. There orientations ensure that the rotation of needle 3010 about central longitudinal axis 3014 cut the adjacent tissue.

As retrieval section 3028 of biopsy needle 3010 is rotated about central longitudinal axis 3014, cutting edge 3030 engages with cellular material located within the biopsy area. Once the cellular material is dislodged from within biopsy area by cutting edge 3030, the cellular material is directed within bore 3026 via the beveled orientation of wall 3056 and preferably also a vacuum force created by the collection reservoir coupled with the proximal end 3016 of biopsy needle 3010. Additionally, multiple crescent cutting apertures 3048 can be disposed in distinct orientations or arrangements. Thus, regardless of how biopsy needle 3010 is manipulated, at least one cutting edge 3030 will engage the tissue of the biopsy area for collection.

Figures 23A, 23C:
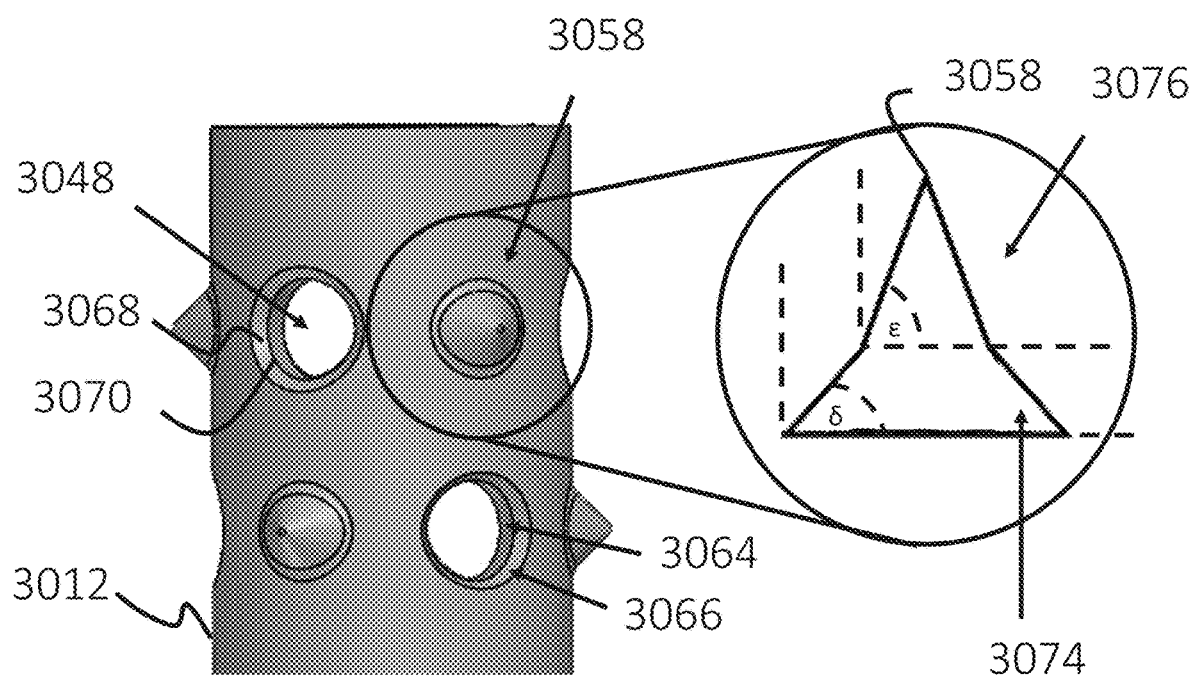
FIG. 23A is a side view of an embodiment of a retrieval section of a biopsy needle used to collect cellular material having a series of alternating conical protrusions and cutting apertures.
FIG. 23C is an elevation diagram of an embodiment of a conical protrusion in FIG. 23A.
Figure 23B:
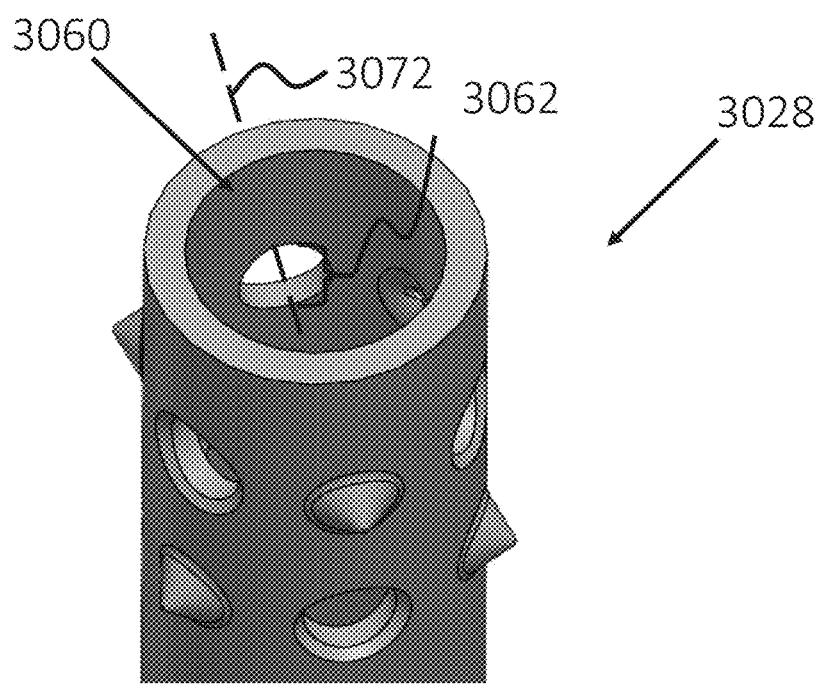
FIG. 23B is a perspective view of an embodiment of a retrieval section of a biopsy needle used to collect cellular material having a series of alternating conical protrusions and cutting apertures.

An embodiment of retrieval section 3028 of biopsy needle 3010 as shown in FIG. 23 includes a plurality of circular cutting apertures 3048 and conical protrusions 3058 configured to cut and tear large portions of cellular material free during manipulation of biopsy needle 3010 within the biopsy area. Cutting apertures 3048 and protrusions 3058 may be randomly disposed of elongated shaft 3012 of biopsy needle 3010 or arranged in a pattern. As depicted in FIGS. 23A and 23B, a patterned embodiment includes alternating cutting apertures 3048 and protrusions 3058 in both a horizontal and vertical direction about elongated shaft 3012. During manipulation of biopsy needle 3010, dislodged cellular material may be collected within bore 3026 via cutting apertures 3048 and bore opening 3060.

Each cutting aperture 3048 is disposed through body 3024 of elongated shaft 3012 from internal surface 3020 to external surface 3022. More particularly, channel 3062 includes first portion 3064 and second portion 3066. First portion 3064 of channel 3062 includes a beveled edge and shares common boundary 3070 with second portion 3066. Channel 3062 includes channel axis 3072 disposed in an orthogonal relationship with central longitudinal axis 3014 of elongated shaft 3012.

Moreover, embodiments of cutting apertures 3048 disposed through body 3024 of retrieval section 3028 may include any other shape, size, or design of cutting apertures 3048 that is in line with any other embodiment of retrieval section 3028 disclosed herein.

Conical protrusions 3058 extend from external surface 3022 of elongated shaft 3012 from first protrusion end 3074 to second protrusion end 3076. First protrusion end 3074 of conical protrusion 3058 has a protrusion angle δ and second protrusion end 3076 has protrusion angle ε. Protrusion angle δ is a smaller angle than protrusion angle ε. Moreover, conical protrusion 3058 is configured to be in mechanical communication with the biopsy area and tears cellular material free, which is then collected through cutting aperture 3048 and/or bore opening 3060.

FIGS. 24A-24D depict an embodiment of retrieval section 3028 of the biopsy needle having a first pair of diametrically opposed cutting apertures 3048A and a second pair of diametrically opposed cutting apertures 3048B. Each cutting aperture 3048 is identical and similarly disposed within body 3024 of elongated shaft 3012 from external surface 3022 to internal surface 3020. In some embodiments, cutting apertures 3048 are not in pairs, but are equidistantly spaced about the circumference of the biopsy needle.

Figure 24A:
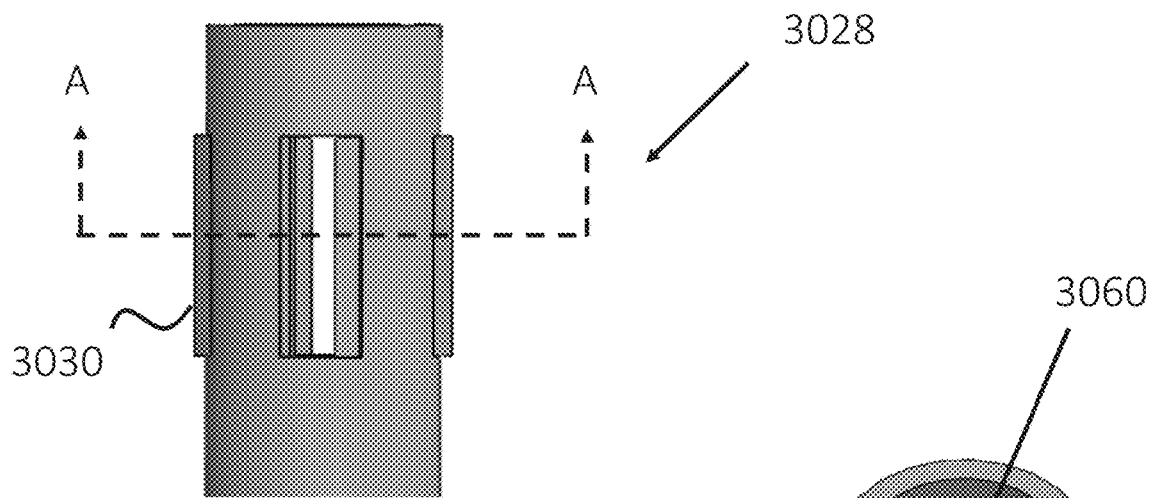
FIG. 24A is a side view of an embodiment of a retrieval section of a biopsy needle having a series of diametrically opposed cutting apertures.
Figure 24B:
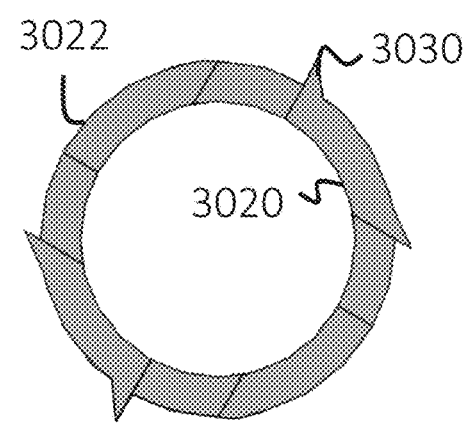
FIG. 24B is a perspective view of an embodiment of a retrieval section of a biopsy needle having a series of diametrically opposed cutting apertures of FIG. 24A.
Figure 24C:
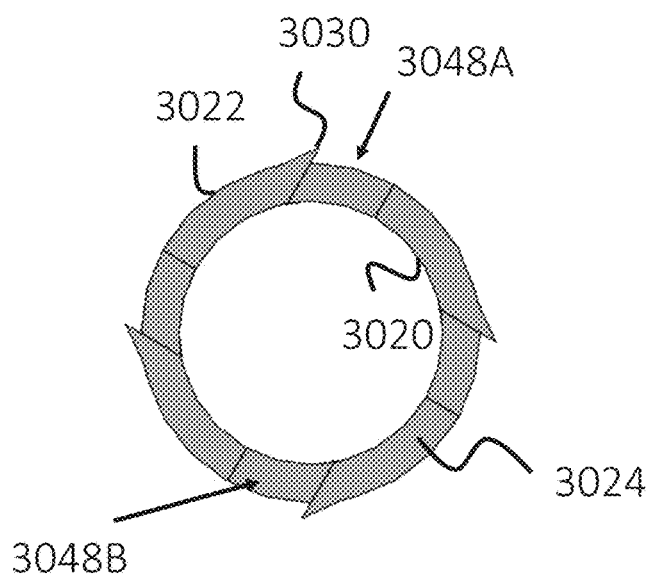
FIG. 24C is a top view of an embodiment of a retrieval section of a biopsy needle having a series of diametrically opposed cutting apertures taken along line A-A in FIG. 24A.
Figure 24D:
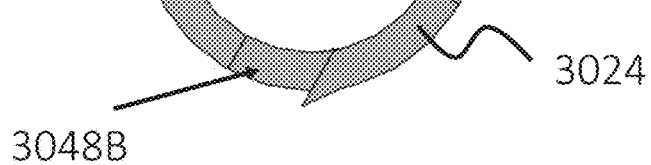
FIG. 24D is a top view of an embodiment of a retrieval section of a biopsy needle having a series of cutting edges extending from the exterior surface of the retrieval section.

Each cutting aperture 3048 includes cutting edge 3030 extending outwardly away from external surface 3022. Each cutting edge 3030 is configured to engage with the tissue within the biopsy area, thereby dislodging the cellular material. Once dislodged, the cellular material is collected within bore 3026 via cutting aperture 3048 and/or bore opening 3060 disposed at distal end 3018 of biopsy needle 3010. Moreover, as depicted in FIG. 24D, a series of cutting edges 3030 extend outwardly from external surface 3022 and are configured to allow the retrieval section 3028 to cut the tissue within the biopsy area when retrieval section 3028 is rotated in both a clockwise and counterclockwise direction.

Figures 25A, 25B:
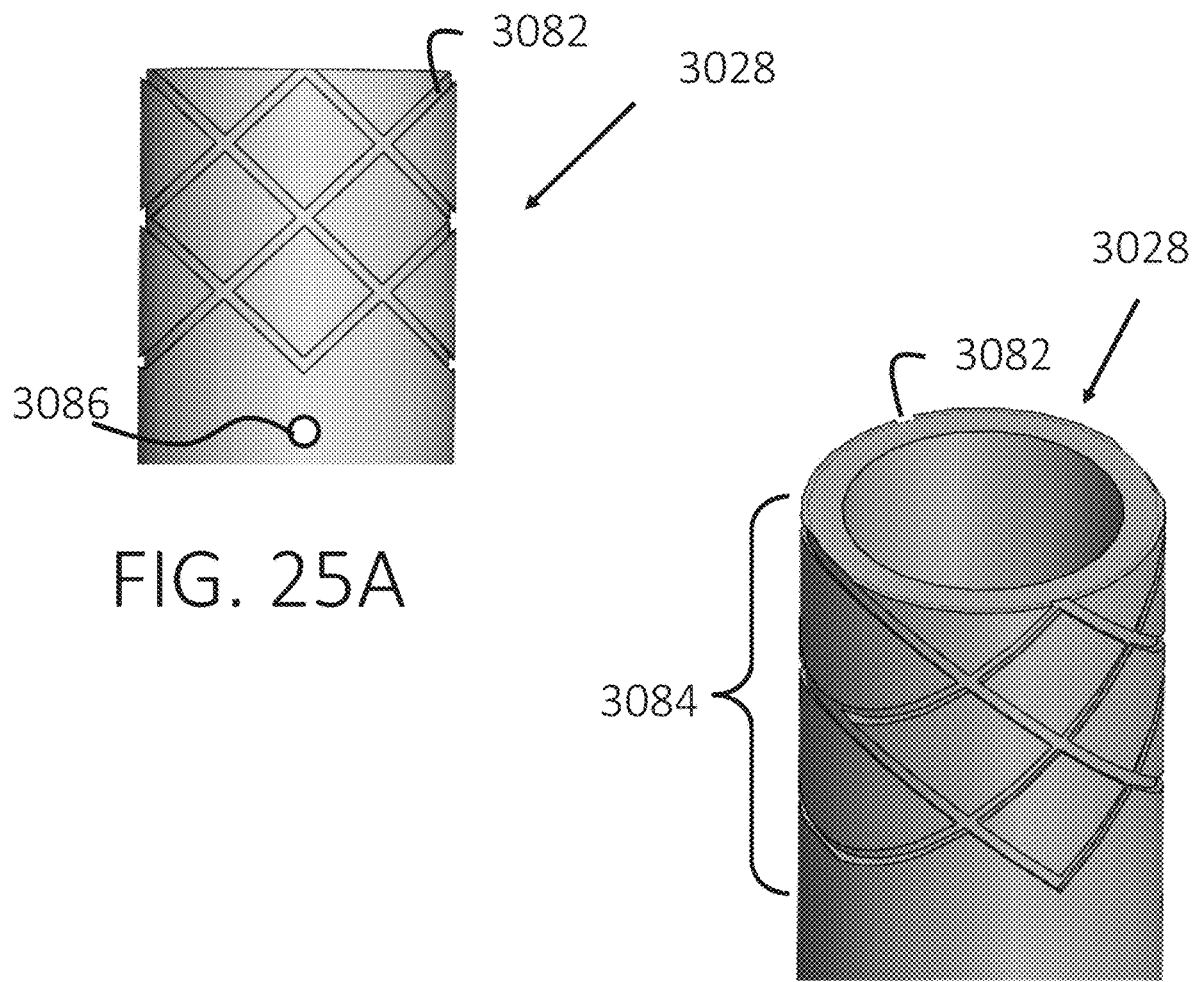
FIG. 25A is a side view of an embodiment of a retrieval section of a biopsy needle having a series of grooves disposed within the body of the elongated shaft.
FIG. 25B is a perspective view of an embodiment of a retrieval section of a biopsy needle having a series of grooves disposed within the body of the elongated shaft.

An embodiment shown in FIGS. 25A-25B includes retrieval section 3028 having chemically etched, or laser cut grooves 3082 disposed on elongated shaft 3012 of biopsy needle 3010. Grooves 3082 are configured to break cellular material free from within the biopsy area during manipulation of biopsy needle 3010. In particular, grooves 3082 may be straight, angled, crossed (as shown), or any other pattern that facilitates the collection of cellular materials. In an embodiment, retrieval section 3028 may include one or more cutting apertures disposed within the body of retrieval section 3028. In such embodiments, the cutting apertures may be in line with any other embodiment of retrieval section 3028 disclosed herein.

The material dislodged during manipulation of retrieval section 3028 is captured through bore opening 3060 and/or collection apertures 3086. Collection apertures 3086 may be disposed above, below, and or within knurling portion 3084 to facilitate the capture of dislodged cellular materials.

Figure 26A:
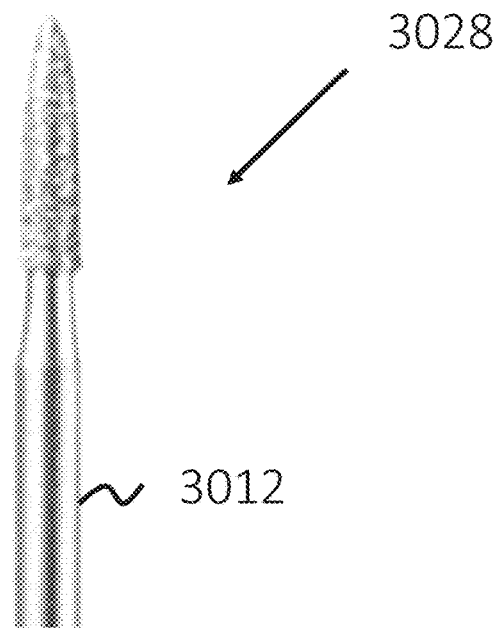
FIG. 26A is a side view of an embodiment of a retrieval section of a biopsy needle having foreign objects disposed on an outer surface of the biopsy needle.
Figure 26B:
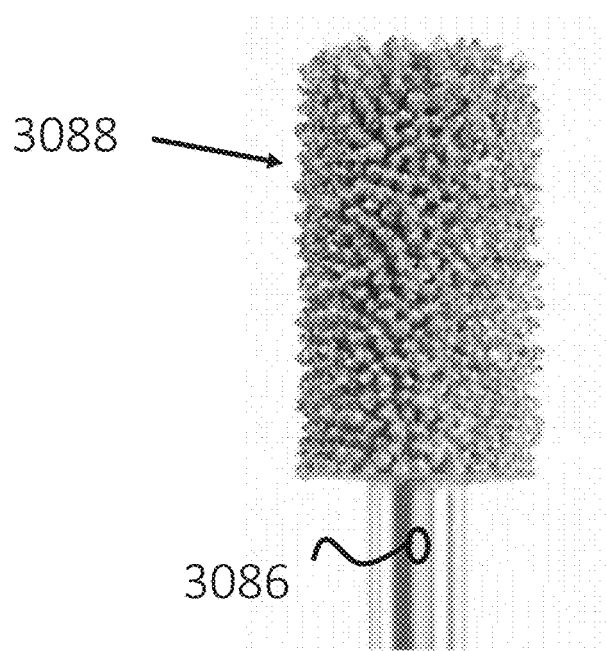
FIG. 26B is a side view of an embodiment of a retrieval section of a biopsy needle having foreign objects disposed on an outer surface of the biopsy needle.

In some embodiments FIGS. 26A and 26B, retrieval section 3028 includes rough grinding surface 3088 disposed on external surface 3022 of retrieval section 3028. In some embodiments, rough grinding surface 3088 can be created by disposing foreign materials on the outer surface 3022 of elongated shaft 3012. Rough grinding surface 3088 is adapted to dislodge cellular material within the biopsy area by grinding cells away from the tissue of the biopsy area. Once cellular material is dislodged by grinding surface 3088, bore 3060 and/or collection apertures 3086 disposed throughout elongated shaft 3012 can be used to facilitate the collection of dislodged cellular materials.

In an embodiment, retrieval section 3028 may include one or more cutting apertures disposed within the body of retrieval section 3028. In such embodiments, the cutting apertures may be in line with any other embodiment of retrieval section 3028 disclosed herein.

Figure 27A:
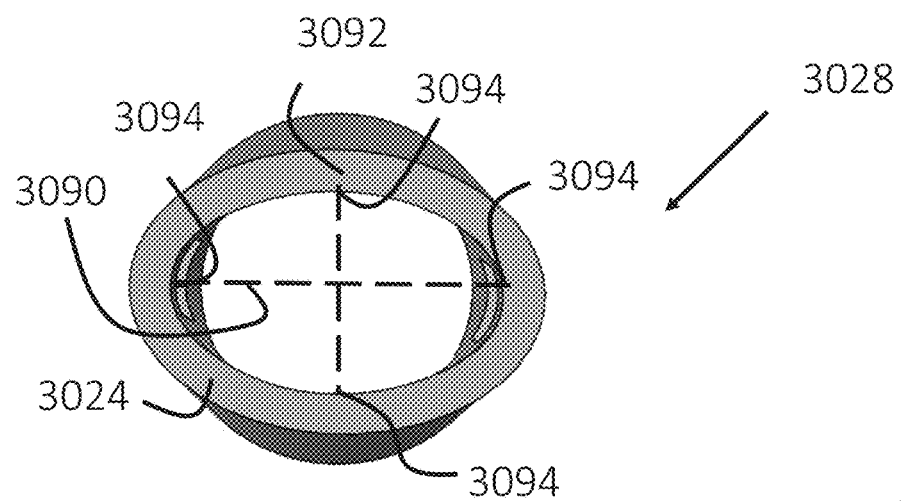
FIG. 27A is a top view of an embodiment of a retrieval section of a biopsy needle having an elliptically shaped bore opening and a cutting aperture disposed within the body of the elongated shaft.
Figure 27B:
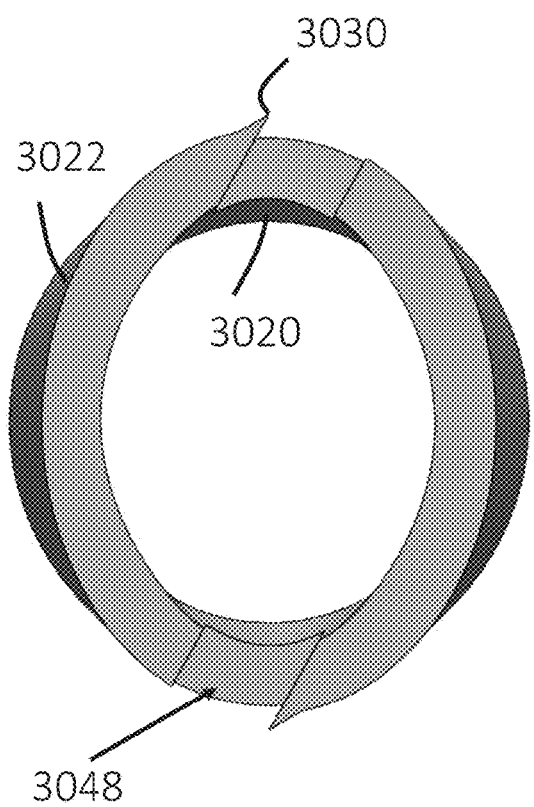
FIG. 27B is a cross-sectional view of an embodiment of a retrieval section of a biopsy needle having an elliptically shaped bore opening and a cutting aperture disposed within the body of the elongated shaft taken along line B-B of FIG. 27C.
Figure 27C:
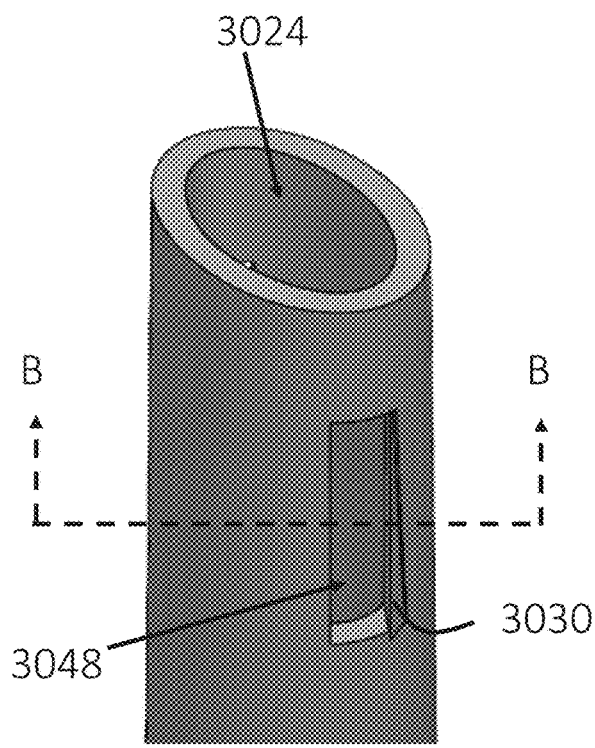
FIG. 27C is a perspective view of an embodiment of a retrieval section of a biopsy needle having an elliptically shaped bore opening and a cutting aperture disposed within the body of the elongated shaft.

In an embodiment shown in FIGS. 27A-27C, retrieval section 3028 of biopsy needle 3010 has an angled tip, for example a 12-degree angle from the central longitudinal axis of the biopsy needle. In some embodiments, retrieval section 3028 has a cross-sectional geometry of an ellipse. The ellipse includes major axis 3090 and minor axis 3092 in an orthogonal relationship with major axis 3090.

Furthermore, retrieval section 3028 of includes a pair of diametrically opposed cutting apertures 3048 disposed at vertices 3094 of major axis 3090 of body 3024 of elongated shaft 3012 from internal surface 3020 to exterior surface 3022. Each cutting aperture includes cutting edge 3030 extending outwardly from external surface 3022 of body 3024. Cutting edge 3030 is configured to engage with the tissue within the biopsy area. Thus, when the biopsy needle is manipulated, cutting edge 3030 dislodges cellular material, which is collected within bore 3026 via cutting apertures 3048 and/or bore opening 3060.

Moreover, embodiments of cutting apertures 3048 disposed through body 3024 of retrieval section 3028 may include any other shape, size, or design of cutting apertures 3048 in line with any other embodiment of retrieval section 3028 disclosed herein.

Figure 28A:
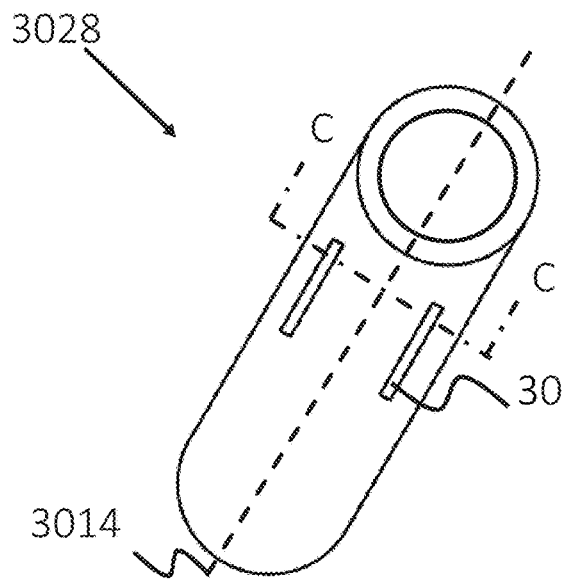
FIG. 28A is a perspective view of an embodiment of a retrieval section of a biopsy needle having cutting apertures disposed within the body of the biopsy needle at the same distance from the terminal end of the retrieval section.
Figure 28B:
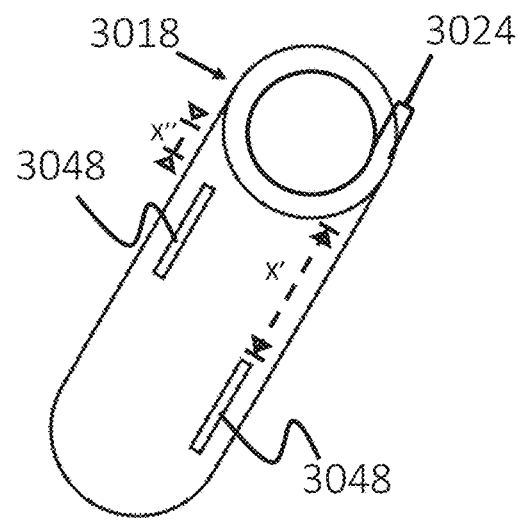
FIG. 28B is a perspective view of an embodiment of a retrieval section of a biopsy needle having cutting apertures disposed within the body of the biopsy needle at a different distance from the terminal end of the retrieval section.
Figure 28C:
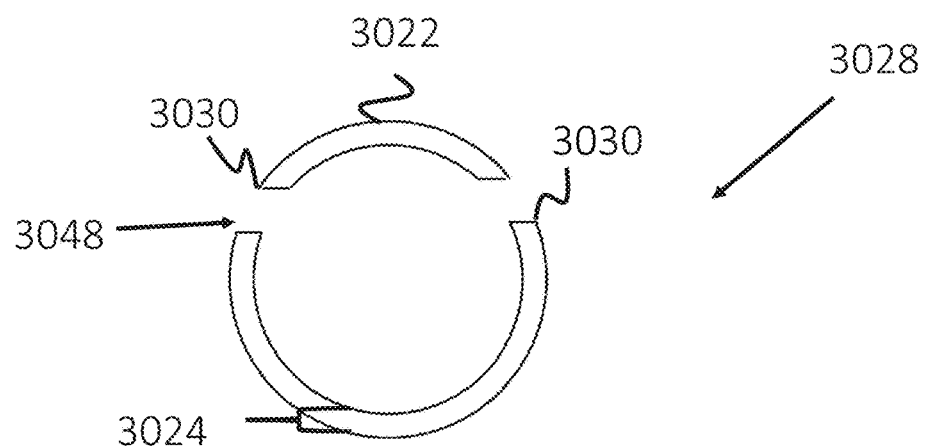
FIG. 28C is a cross-sectional view of an embodiment of a retrieval section of a biopsy needle taken along line C-C of FIG. 28A having cutting apertures disposed within the body of the biopsy needle.

In some embodiments, as shown in FIGS. 28A-28C, retrieval section 3028 has a cross-sectional geometry of a circle; however, it is appreciated that various cross-sectional geometries may be provided depending on the specific needs of the biopsy needle during the procedure. Furthermore, cutting apertures 3048 are disposed within body 3024. Specifically, cutting apertures 3048 may be disposed from one another at the same distance from terminal end 29 (see FIG. 28A) or disposed at different distances (x', x") from terminal end 29 of retrieval section 3028 (see FIG. 28B).

Additionally, cutting edges 3030 are flush with and follow the curvature (i.e., circumference) of external surface 3022 of retrieval section 3028. In such embodiments, the manipulation of retrieval section 3028 laterally in an orthogonal relationship with axis 3014 forces tissues within the biopsy area in cutting apertures 3048. Thus, upon rotation of retrieval section 3028 about axis 3014 in either a clockwise or counterclockwise rotation, at least one of the cutting edges 3030 sheers off the tissue disposed within cutting aperture 3048 for sample collection.

Moreover, embodiments of cutting apertures 3048 disposed within body 3024 of retrieval section 3028 may include any other shape, size, or design of cutting apertures 3048 that are in line with any other embodiment of retrieval section 3028 disclosed herein.

Figure 29A:
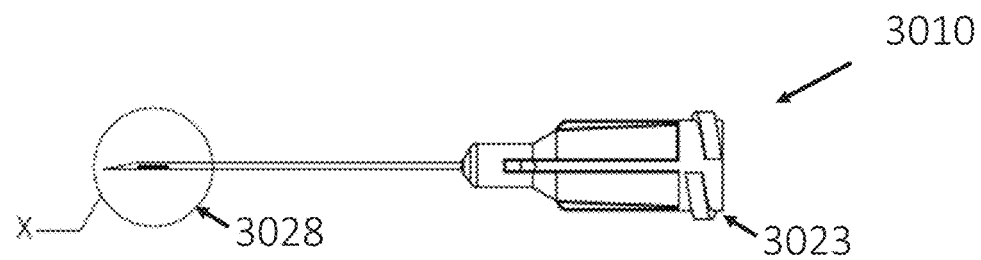
FIG. 29A is a side view of an embodiment of a biopsy needle.
Figure 29B:
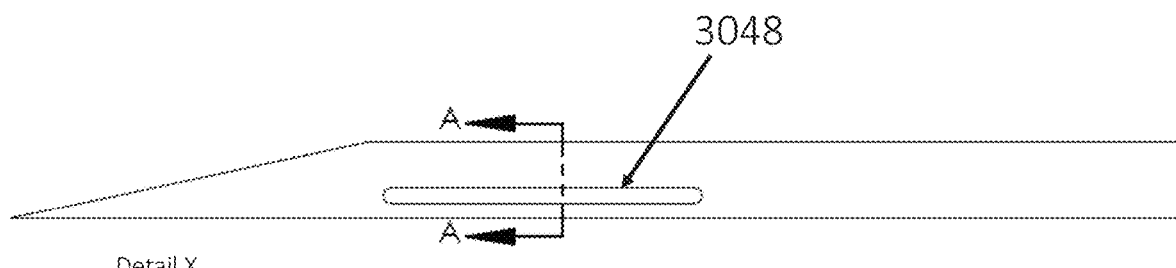
FIG. 29B is a side view of Detail X in FIG. 29A.
Figure 29C:
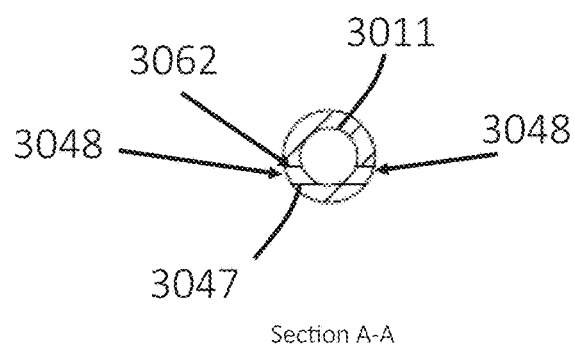
FIG. 29C is a cross-sectional view of an embodiment of a retrieval section of a biopsy needle taken along line A-A of FIG. 29A.

Some embodiments, a depicted in FIG. 29 include multiple cutting apertures 3048 with each disposed on opposite sides of biopsy needle 3010. In some embodiments, outer lateral edge 3027 of channel 3062 is tangentially aligned with the interior surface 3011 of biopsy needle 3010.

Figure 30A:
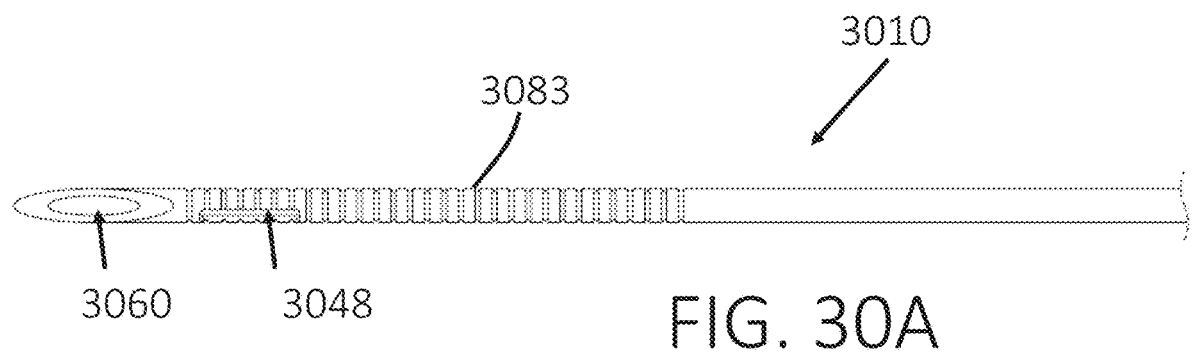
FIG. 30A is a side view of an embodiment of a biopsy needle.
Figure 30B:
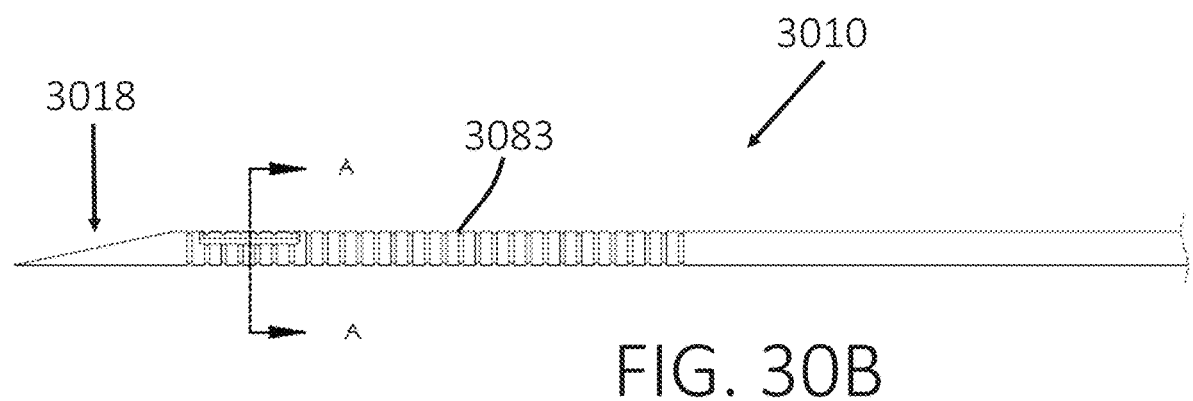
FIG. 30B is a side view of an embodiment of a biopsy needle.
Figure 30C:
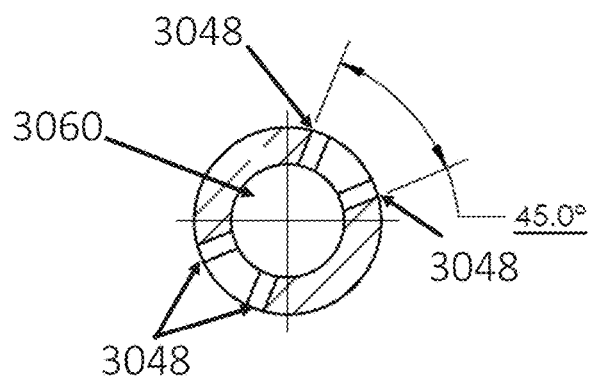
FIG. 30C is a cross-sectional view of an embodiment of a retrieval section of a biopsy needle taken along line A-A of FIG. 30A.

As illustrated in FIG. 30, some embodiments further include a plurality of annular grooves 3083. Grooves 3083 are configured to break cellular material free from within the biopsy area during manipulation of biopsy needle 3010. Similar to grooves 3082 in FIG. 25, grooves 3083 may be straight and perpendicular to the central longitudinal axis of needle 3010 as shown in FIG. 30 or they may be angled, crossed, or have any other pattern that facilitates the collection of cellular materials. In some embodiments, retrieval section grooves are located in the same general area as cutting apertures 3048, however, some embodiments may have grooves 3083 longitudinally offset from cutting apertures 3048.

Figure 31A:
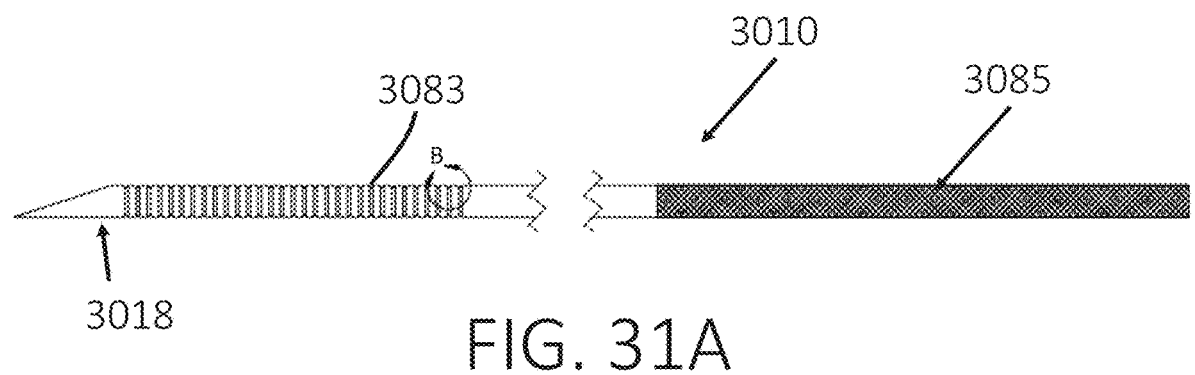
FIG. 31A is a side view of an embodiment of a biopsy needle.
Figure 31B:
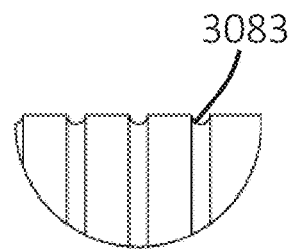
FIG. 31B is a side view of Detail B in FIG. 31A.

Moreover, some embodiments may include grooves 3083 without include cutting apertures 3048 as depicted in FIG. 31. In such embodiments, tissue enters bore channel 3060 in biopsy needle 3010 through distal end 3018.

Some embodiments include biopsy needle 3010 having a proximal section with knurling 3085 or other friction increasing features. The friction increasing features on the proximal portion aid in retaining a secure connection with needle 3010.

Referring back to FIG. 30C, the depicted embodiment illustrates the circumferential spacing of cutting apertures 3048 about needle 3010. The depicted embodiment includes two pairs of diametrically opposed cutting apertures 3048 with the closest cutting apertures 3048 circumferentially offset roughly 45 degrees. As depicted, the angular offset is from the furthest edges of the two adjacent cutting apertures 3048, however, alternative points on the two adjacent cutting apertures 3048 may establish the 45-degree separation.

In some embodiments, the circumferential spacing between two adjacent cutting apertures is between 5 and 90 degrees. In some embodiments, the circumferential spacing between two adjacent cutting apertures is between 5 and 180 degrees. It should also be understood that the circumferential spacing of cutting apertures may apply to the other embodiments disclosed herein.

Method of Manufacturing

Figure 32:
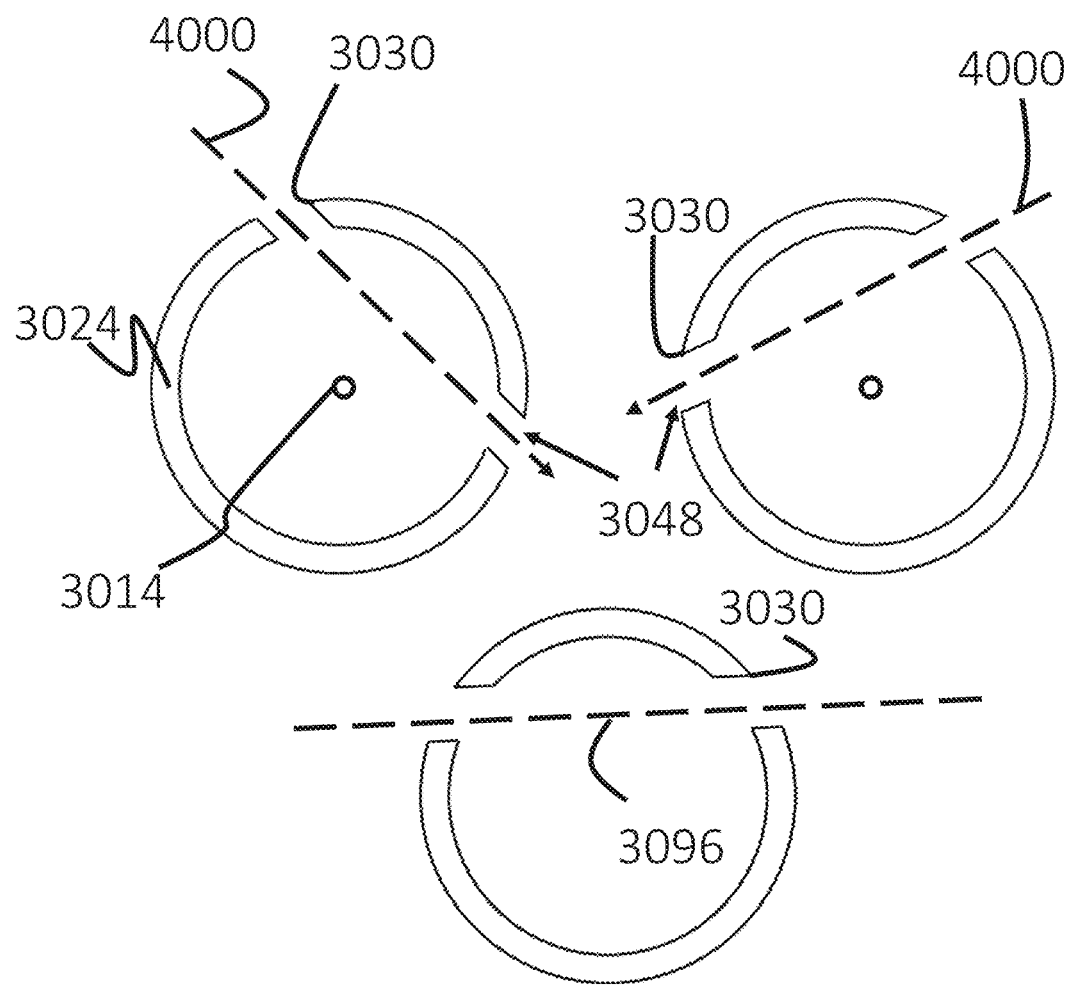
FIG. 32 is a cross-sectional view of the elongated shaft of the biopsy needle depicting a laser cutting a pair of cutting apertures within the body of the elongated shaft.

FIG. 32 depicts a method of manufacturing an embodiment of biopsy needle 3010 utilizing a novel methodology that results in biopsy needle 3010 having multiple cutting edges 3030 (or cutting apertures 3048). Each cutting edge 3030 is manufactured in pairs, such that no matter which direction biopsy needle 3010 is rotated about its central longitudinal axis 3014, cutting edge 3030 engages tissue within the biopsy area. In an embodiment, cutting edges 3030 are manufactured using a high-powered laser. In particular, the laser is directed toward body 3024 of elongated shaft 3012 at an angle along secant line 3096. In an embodiment, one or more laser cuts 4000 made be made along one or more secant lines 3096 to manufacture multiple cutting apertures 3048 within body 3024 of elongated shaft 3012, such as above or below previous laser cut(s).

Figure 33A:
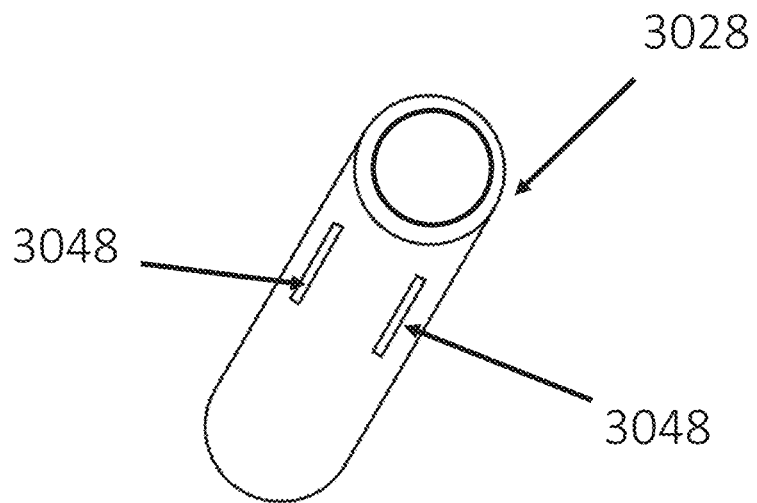
FIG. 33A is a perspective view of an embodiment of a biopsy needle in which the cutting apertures are each disposed the same distance from the retrieval section.
Figure 33B:
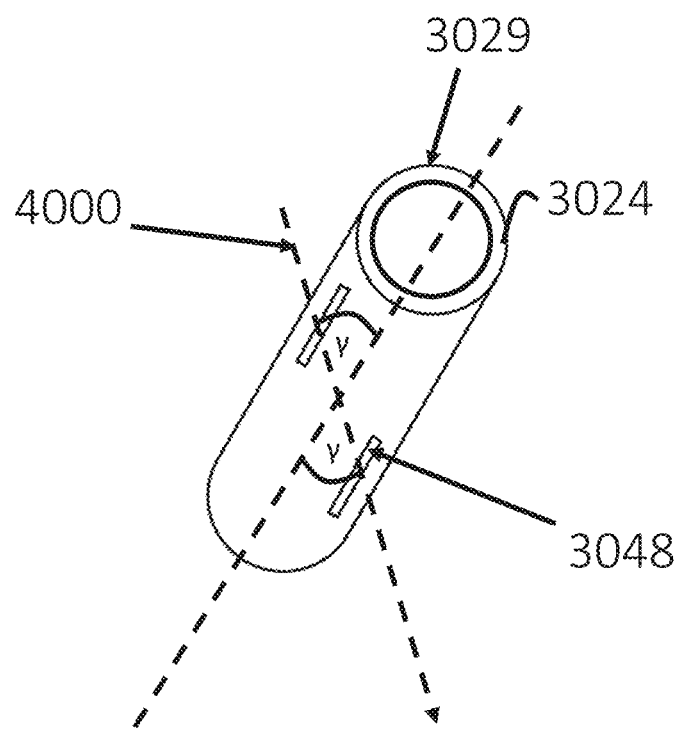
FIG. 33B is a perspective view of an embodiment of a biopsy needle in which the cutting apertures are disposed at different distances from the retrieval section.
Figure 33C:
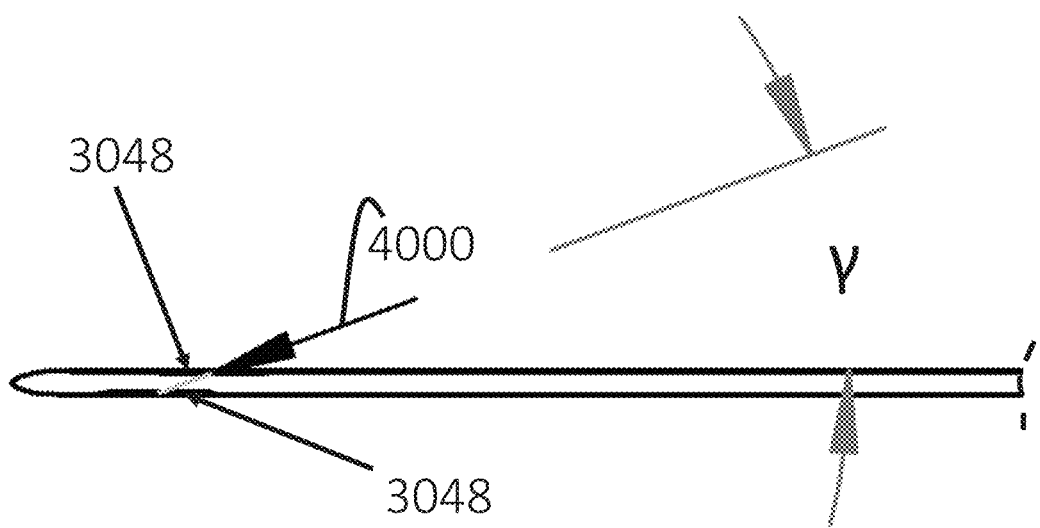
FIG. 33C is a side view of an embodiment of a biopsy needle in which the cutting apertures are disposed at different distances from the retrieval section.

FIG. 33A depicts an embodiment of the novel method of manufacturing in which laser cuts 4000 are formed within body 3024 at the same distance from distal end 3018 of biopsy needle 3010. Alternatively, FIGS. 33B and 33C depict an embodiment of the novel method of manufacturing in which laser cuts 4000 are formed within body 3024 of elongated shaft 3012 at angle γ, such that cutting apertures 3048 are formed within body 3024 at different distances from distal end 29 of biopsy needle 3010. By manufacturing multiple cutting apertures 3048 of biopsy needle 3010 with a single pass of the laser, the overall manufacturing time of biopsy needle 3010 is significantly reduced.

While the particular device is herein shown and described in detail, it is to be understood that the subject matter which is encompassed by the present invention is limited only by the claims.

Components included in one embodiment can be used in other embodiments in any appropriate combination. For example, any of the various components described herein and/or depicted in the Figures may be combined, interchanged, or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An endobronchial ultrasound needle (EBUS) assembly, comprising:
    a housing with at least first and second segments coupled telescopically;
    at least one hollow needle supported by the housing, the needle including:
    a main body extending between a proximal end and a distal end;
    a cutting tip located at the distal end;
    a central longitudinal axis extending between the proximal and distal ends;
    a first cutting aperture disposed through the main body;
    a second cutting aperture disposed through the main body;
    the first and second cutting apertures longitudinally spaced in a proximal direction from the distal end of the main body, such that there is a continuous portion of the main body between the first and second cutting apertures and the distal end of the main body;
    wherein the cutting tip located at the distal end is a beveled cutting tip;
    wherein telescopically adjusting the first and second segments alters a length of protrusion of the needle distally beyond the housing;
    at least one motor in the housing,
    wherein the at least one motor is operably coupled to the needle to cause the needle to rotate;
    a luer fitting passing through a motor mount to rotatably connect to the proximal end of the needle thereby establishing a fluid channel between the needle and an external component:
    an endoscope adapter located proximate a distal end of the needle, the endoscope adapter having a spring-loaded slide mechanism for engaging the needle with an endoscope:
    and wherein the needle rotates without rotating the luer fitting.

2. The EBUS assembly of claim 1, comprising a sheath surrounding the needle.

3. The EBUS assembly of claim 1, wherein the housing comprises at least a third segment coupled telescopically with the second segment.

4. The EBUS assembly of claim 1, comprising a power supply in the housing connected to the motor to energize the motor.

5. The EBUS assembly of claim 1, comprising a manipulable actuator on the housing to energize the motor.

6. The EBUS assembly of claim 1, comprising a first manipulable mechanical stop on the housing and movable from a first position, in which the first and second segments can telescope relative to each other, and a second position, in which the first and second segments cannot telescope relative to each other.

7. The EBUS assembly of claim 6, wherein the first manipulable mechanical stop comprises a thumb screw.

8. The EBUS assembly of claim 6, comprising a second manipulable mechanical stop on the housing and movable to lock the second segment to a third segment.

9. The EBUS assembly of claim 1, further comprising a control circuit configured to rotate the needle in a first direction when the motor is energized, and after a predetermined time period, rotate the needle in an opposite direction.

10. The EBUS assembly of claim 1, further including:
    the first cutting aperture having a rectangular shape with a long end of the rectangular shape extending parallel to the central longitudinal axis of the needle; and
    the second cutting aperture having a rectangular shape identical to the first cutting aperture with a long end of the rectangular shape extending parallel to the central longitudinal axis of the needle.

11. The EBUS assembly of claim 1, further including each of the first and second cutting apertures creating a channel with a central axis extending from an exterior surface of an interior surface of the main body of the needle, wherein the central axes of the channels are aligned.

12. The EBUS assembly of claim 1, wherein the cutting tip of the needle is comprised of a beveled opening.

13. The EBUS assembly of claim 1, wherein the first cutting aperture is diametrically opposed to the second cutting aperture.

14. The device of claim 1, wherein each of the cutting apertures are defined by a boundary circumscribing the aperture and the boundary is generallyflush with an exterior surface of the main body.

15. The device of claim 1, wherein each cutting aperture isthe a same distance from the distal end of the needle.

16. The device of claim 1, wherein the first cutting aperture is longitudinally spaced from the second cutting aperture, such that the two cutting apertures are at different distances from the distal end of the needle.

17. The device of claim 1, wherein each cutting aperture includes a beveled channel wall extending between the interior and an exterior surface of the main body of the needle to direct tissue into the interior of the needle.

18. The device of claim 1, wherein each of the cutting apertures includes an outwardly, laterally extending flange relative to the central longitudinal axis of the needle.

19. The device of claim 1, wherein a portion of the needle proximal to the of the cutting apertures includes a plurality of annular grooves circumscribing an exterior surface of the needle.

20. The device of claim 1, further including:
    a third cutting aperture disposed through the main body, wherein the third cutting aperture has a rectangular shape with a long end of the rectangular shape extending parallel to the central longitudinal axis of the needle;
    a fourth cutting aperture disposed through the main body, wherein the fourth cutting aperture has a rectangular shape identical to the first cutting aperture with a long end of the rectangular shape extending parallel to the central longitudinal axis of the needle;
    the third and fourth cutting apertures longitudinally spaced in the proximal direction from the distal end of the main body, such that the continuous portion of the main body is between the third and fourth cutting apertures and the distal end of the main body;
    the third and fourth cutting apertures diametrically opposed from each other about the main body of the needle; and the third cutting aperture is circumferentially spaced from the first cutting aperture by 45 degrees.

\* \* \* \* \*